United States Patent
Oakley et al.

(10) Patent No.: US 9,854,988 B2
(45) Date of Patent: Jan. 2, 2018

(54) APPARATUS, SYSTEMS AND METHODS FOR RECEIVING SIGNALS FROM A HUMAN SUBJECT'S BRAIN

(71) Applicant: WAVi Co., Boulder, CO (US)

(72) Inventors: David Oakley, Boulder, CO (US); Edward Altshuler, Dacono, CO (US); Scott Seamans, Newport Beach, CA (US)

(73) Assignee: WAVI CO, Boulder, CO (US)

(*) Notice: Subject to any disclaimer, the term of this patent is extended or adjusted under 35 U.S.C. 154(b) by 0 days.

(21) Appl. No.: 15/163,292

(22) Filed: May 24, 2016

(65) Prior Publication Data

US 2016/0354005 A1 Dec. 8, 2016

Related U.S. Application Data

(60) Provisional application No. 62/170,104, filed on Jun. 2, 2015, provisional application No. 62/196,066, filed on Jul. 23, 2015.

(51) Int. Cl.
*A61B 5/0478* (2006.01)
*A61B 5/0476* (2006.01)
*A61B 5/00* (2006.01)

(52) U.S. Cl.
CPC .......... *A61B 5/0478* (2013.01); *A61B 5/0476* (2013.01); *A61B 5/6803* (2013.01); *A61B 5/6814* (2013.01); *A61B 5/683* (2013.01); *A61B 5/6843* (2013.01); *A61B 2560/0443* (2013.01)

(58) Field of Classification Search
CPC ... A61B 5/0478; A61B 5/6803; A61B 5/6814; A61B 5/683; A61B 5/6831; A61B 2560/0443; A61B 2562/046
USPC .......................................... 600/383, 544–545
See application file for complete search history.

(56) References Cited

U.S. PATENT DOCUMENTS

| | | | | |
|---|---|---|---|---|
| 3,508,541 A | * | 4/1970 | Westbrook | A61B 5/0478 600/383 |
| 4,632,122 A | | 12/1986 | Johansson et al. | |
| 4,923,469 A | * | 5/1990 | Frachet | A61F 11/04 600/383 |
| 5,479,934 A | * | 1/1996 | Imran | A61B 5/0017 600/390 |

(Continued)

FOREIGN PATENT DOCUMENTS

| | | |
|---|---|---|
| JP | 2013078419 A | 5/2013 |
| WO | 0051028 A1 | 8/2000 |
| WO | 2009079377 A2 | 6/2009 |

*Primary Examiner* — Lee S Cohen
*Assistant Examiner* — Erin M Cardinal
(74) *Attorney, Agent, or Firm* — E. Randall Smith; E. Randall Smith, PC

(57) ABSTRACT

Apparatus and methods for use in connection with receiving signals from a human subject's head through the scalp thereof includes a removable headset having a plurality of electrode stations and intermediate portions. Each electrode station includes an electrode aperture extending therethrough and a biasing flap coupled to the headset and at least partially aligned over the associated electrode aperture. A plurality of removable electrodes is releasably engageable with the headset and configured to be releasably suspended within the electrode apertures and biased between the headset and the subject's head by the associated biasing flaps.

59 Claims, 16 Drawing Sheets

(56) References Cited

U.S. PATENT DOCUMENTS

| | | | |
|---|---|---|---|
| 6,161,030 A * | 12/2000 | Levendowski | A61B 5/0478 600/383 |
| 6,167,298 A | 12/2000 | Levin | |
| 6,195,576 B1 | 2/2001 | John | |
| 6,381,481 B1 | 4/2002 | Levandowski et al. | |
| 6,574,513 B1 * | 6/2003 | Collura | A61B 5/6803 600/153 |
| 6,912,414 B2 | 6/2005 | Tong | |
| 8,924,230 B2 | 12/2014 | Oakley et al. | |
| 8,930,212 B2 | 1/2015 | Oakley et al. | |
| 8,930,218 B1 | 1/2015 | Oakley et al. | |
| 2001/0044573 A1 * | 11/2001 | Manoli | A61B 5/0478 600/383 |
| 2002/0188216 A1 | 12/2002 | Kayyali et al. | |
| 2003/0233250 A1 | 12/2003 | Joffe et al. | |
| 2004/0236226 A1 * | 11/2004 | Maki | A61B 5/0261 600/473 |
| 2005/0107716 A1 | 5/2005 | Eaton et al. | |
| 2007/0004978 A1 * | 1/2007 | Ponton | A61B 5/0478 600/372 |
| 2007/0093706 A1 | 4/2007 | Gevins et al. | |
| 2007/0225585 A1 * | 9/2007 | Washbon | A61B 5/0478 600/393 |
| 2008/0027345 A1 * | 1/2008 | Kumada | A61B 5/0478 600/383 |
| 2009/0030298 A1 * | 1/2009 | Matthews | A61B 5/6843 600/383 |
| 2009/0088619 A1 | 4/2009 | Turner et al. | |
| 2009/0156925 A1 * | 6/2009 | Jin | A61B 5/0478 600/396 |
| 2010/0017225 A1 | 1/2010 | Oakley et al. | |
| 2010/0125190 A1 * | 5/2010 | Fadem | A61B 5/0478 600/383 |
| 2011/0015503 A1 | 1/2011 | Joffe et al. | |
| 2012/0330125 A1 * | 12/2012 | Wilson | A61B 5/0408 600/383 |
| 2013/0172722 A1 | 7/2013 | Ninane et al. | |
| 2013/0253300 A1 * | 9/2013 | Fadem | A61B 5/0484 600/383 |
| 2014/0213874 A1 * | 7/2014 | Tong | A61B 5/6803 600/383 |

\* cited by examiner

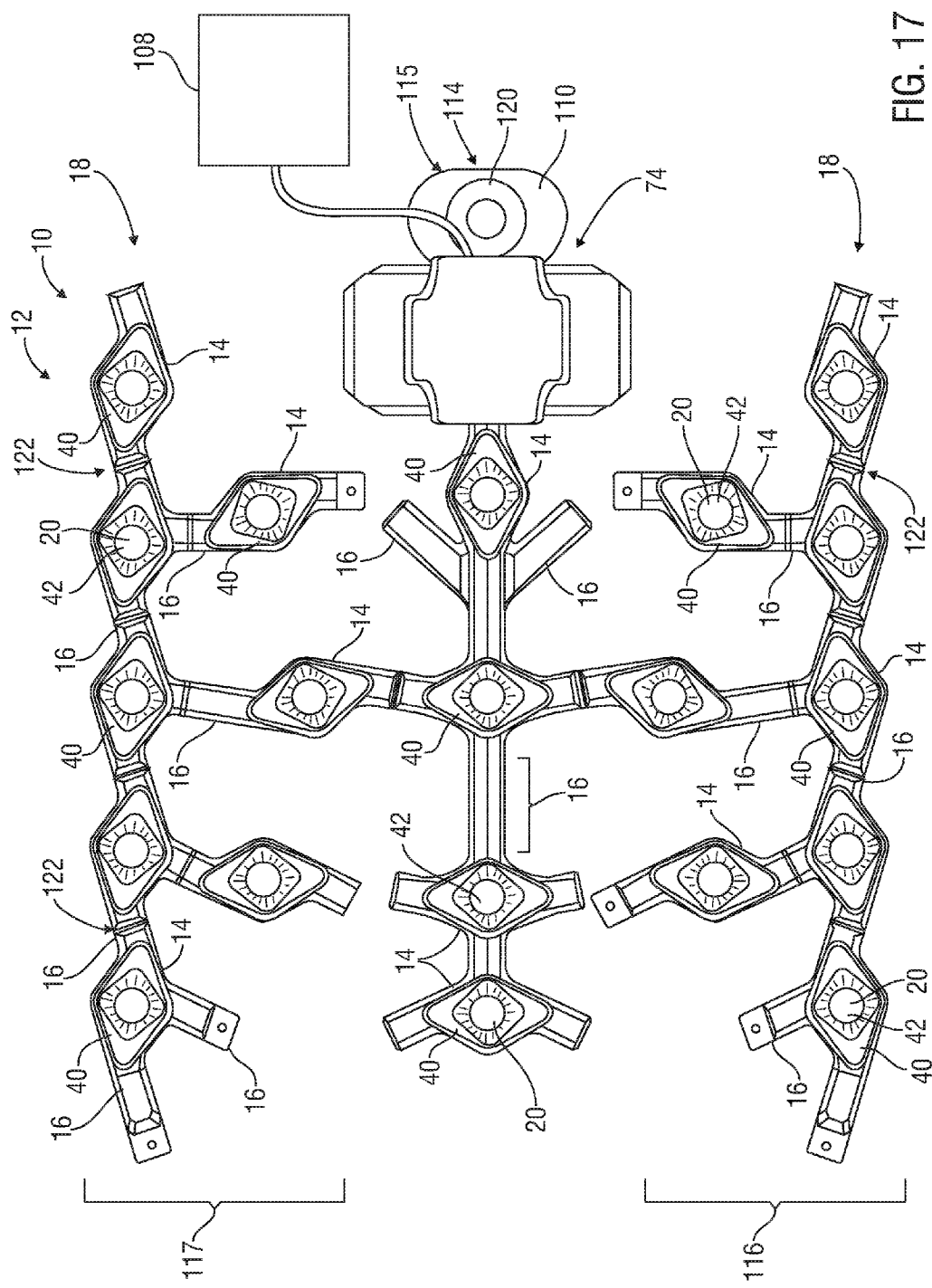

APPARATUS, SYSTEMS AND METHODS FOR RECEIVING SIGNALS FROM A HUMAN SUBJECT'S BRAIN

The present application claims priority to U.S. Provisional Patent Application Ser. No. 62/170,104 filed on Jun. 2, 2015 and entitled "Electrode Headset System", and U.S. Provisional Patent Application Ser. No. 62/196,066 filed on Jul. 23, 2015 and entitled "Electrode Headset System and Related Apparatus, Systems, Methods, Compositions and Articles of Manufacture", the entire contents of which are hereby incorporated by reference herein in their entireties.

FIELD OF THE DISCLOSURE

The present disclosure relates generally to apparatus, systems and methods for receiving signals from a human subject's brain.

BACKGROUND

Taking brain activity data, brainwave measurements or the like, such as with known (electroencephalographic) EEG technology, historically required attaching electrodes to shaved portions of a subject's scalp area and customizing the placement of each electrode for high conductivity in order to receive useful signals during the test. One solution to shaving a patient's head was to sew electrodes to an elastic cap that is fit tightly onto the subject's head, each electrode terminating permanently in a wire that is bundled with other wires and routed to an electrical connector.

Existing technology for receiving signals from a subject's brain are believed to possess one or more potential disadvantages. For example, in some instances with the use of known EEG headsets, an electrode positioned over an uneven, or indented, portion of the subject's head may not abut or conform thereto sufficient to conduct an electrical signal from the scalp to a measuring device that is useful for the test. For another example, the hair style of the subject (e.g. cornrows) may not allow sufficient electrical conductivity from the scalp to each electrode. For still a further example, the solid cap typically covers the entire scalp area of the subject and therefore does not allow the administrator of the test to visually inspect or adjust the position of the cap or individual electrodes to make meaningful, timely adjustments to achieve sufficient electrical contact. In many cases, the caps fit tightly over the subject's hair and scalp and become soiled with dirt, oil, germs, etc., which may be transferred to subsequent subjects using the same headset. For still another possible example, the sewn-in electrodes may not be rotated or moved for improved contact and may not be easily replaced with a different size or style that better matches a subject's physiology. Yet other potential disadvantages of known technology will be apparent from the description below.

It should be understood that the above-described features, capabilities and disadvantages are provided for illustrative purposes only and are not intended to limit the scope or subject matter of the appended claims or those of any related patent application or patent. Thus, none of the appended claims or claims of any related application or patent should be limited by the above discussion or construed to address, include or exclude each or any of the above-cited features, capabilities or disadvantages merely because of the mention thereof herein.

Accordingly, there exists a need for improved apparatus, systems and methods useful for receiving signals from a human subject's brain having one or more of the attributes or capabilities described or shown in, or as may be apparent from, the other portions of this disclosure.

BRIEF SUMMARY OF THE DISCLOSURE

In some embodiments, the present disclosure involves apparatus for use in connection with receiving electroencephalographic (EEG) signals from a human subject's head through the scalp thereof. The apparatus includes a removable headset arranged and adapted to extend at least partially around the subject's head over at least part of the subject's scalp. The headset includes an inner side and an outer side, the inner side being closest to the subject's scalp when the headset is positioned least partially around the subject's head. The headset includes a plurality of electrode stations and a plurality of intermediate portions. The intermediate portions extend between the electrode stations and are shaped and sized to form open spaces therebetween. Each electrode station includes an electrode aperture extending therethrough from the outer side to the inner side of the headset. The headset further includes a plurality of non-conductive biasing flaps, each biasing flap being coupled to the headset and at least partially aligned over one of the electrode apertures. The headset further includes at least one EEG signal transmission wire associated with the electrode stations for receiving EEG signals.

In these embodiments, a plurality of removable electrodes are releasably engageable with the headset and useful to facilitate the transmission of EEG signals from the subject's head to at least one EEG signal transmission wire of the headset during use of the headset. Each electrode includes a top end, bottom end and at least one side extending therebetween. Each electrode is configured to be releasably suspended within one of the electrode apertures and biased between the headset and the subject's head by the associated biasing flap. A plurality of electrically-conductive, electrode covers constructed at least partially of flexible, liquid-absorbing material are arranged and adapted to receive EEG signals from the subject's head and transmit such signals to at least one the EEG signal transmission wire of the headset during use of the headset. Each electrode cover at least partially encapsulates an electrode and is laden with electrically-conductive liquid during use of the headset. Each biasing flap is configured to bias the associated electrode cover into contact with the subject's head to allow the associated cover to receive EEG signals from the subject's head.

In at least one embodiment, a method of using the above-referenced apparatus includes releasably suspending the plurality of electrodes along with their associated electrically-conductive, liquid laden, electrode covers within the respective associated electrode apertures in the headset. The headset is placed on the subject's head. At least some of the biasing flaps bias their associated electrodes in the direction of the subject's head independent of the other electrodes in the headset. At least some of the electrode covers receive useful signals from the subject's head and transmit the received signals to at least one EEG signal transmission wire in the headset.

In various embodiments, the present disclosure involves apparatus for use in connection with receiving electroencephalographic (EEG) signals from a human subject's head through the scalp thereof. The apparatus includes a removable headset arranged and adapted to extend at least partially around the subject's head over at least part of the subject's scalp, the headset including an inner side and an outer side, the inner side being closest to the subject's scalp when the headset is positioned least partially around the subject's head. The headset includes a plurality of electrode stations and a plurality of intermediate portions extending between the electrode stations and shaped and sized to form open spaces therebetween. Each electrode station includes an electrode aperture extending therethrough from the outer side to the inner side of the headset. The headset further includes a plurality of non-conductive biasing flaps, each biasing flap being coupled to the headset and at least partially aligned over one of the electrode apertures. The headset further includes at least one EEG signal transmission wire associated with the electrode stations for receiving EEG signals.

In these embodiments, a plurality of removable electrodes are releasably engageable with the headset and useful to facilitate the transmission of EEG signals from the subject's head to at least one the EEG signal transmission wire of the headset during use of the headset. Each electrode includes a top end, bottom end, at least one side extending therebetween and at least one protrusion extending outwardly from at least one of the sides. The protrusion is arranged and adapted to selectively position the associated electrode relative to the associated electrode aperture. Each electrode is configured to be releasably suspended within one of the electrode apertures and biased towards the subject's head by the associated biasing flap.

In at least one embodiment, a method of using the immediately above-referenced apparatus includes releasably suspending the plurality of electrodes within the respective associated electrode apertures in the headset. The headset is placed on the subject's head. At least some of the biasing flaps bias their associated electrodes in the direction of the subject's head independent of the other electrodes in the headset.

The present disclosure also includes embodiments of an apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset includes a plurality of electrode stations and a plurality of intermediate portions extending between the electrode stations and shaped and sized to form open spaces therebetween. Each electrode station has an electrode aperture extending therethrough from the outer side to the inner side of the headset. The headset further includes a plurality of biasing flaps, each biasing flap being coupled to the headset and at least partially aligned over one of the electrode apertures. The headset further includes at least one EEG signal transmission wire associated with the electrode stations for receiving EEG signals.

In these embodiments, a plurality of removable electrodes releasably are engageable with the headset and useful to facilitate the transmission of EEG signals from the subject's head to at least one the EEG signal transmission wire of the headset during use of the headset. Each electrode includes a top end, bottom end, at least one side extending therebetween and at least one protrusion extending outwardly from at least one side. The protrusion is arranged and adapted to selectively position the associated electrode relative to the associated electrode aperture. Each electrode is configured to be releasably suspended within one of the electrode apertures and biased towards the subject's head by the associated biasing flap. Each biasing flap includes a flap hole at least partially aligned over the associated electrode aperture. Each flap hole includes at least one groove configured to selectively retain at least one the protrusion of the associated electrode. When at least one protrusion is selectively secured in the groove of its associated biasing flap, the electrode is configured to be moveable with the biasing flap relative to the electrode aperture during use of the headset.

The present disclosure also includes embodiments of apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side. The inner side is closest to the subject's scalp when the headset is positioned least partially around the subject's head. The headset includes a plurality of electrode stations and a plurality of intermediate portions extending between the electrode stations and shaped and sized to form open spaces therebetween. Each electrode station includes an electrode aperture extending therethrough from the outer side to the inner side of the headset.

In these embodiments, the headset further includes a plurality of biasing flaps. Each biasing flap is directly coupled to the headset and at least partially aligned over one of the electrode apertures. The headset further includes at least one EEG signal transmission wire associated with the electrode stations for receiving EEG signals. A plurality of removable electrodes are releasably engageable with the headset and useful to facilitate the transmission of EEG signals from the subject's head to at least one the EEG signal transmission wire of the headset during use of the headset. Each electrode includes a top end, bottom end and at least one side extending therebetween. Each electrode is configured to be releasably suspended within one of the electrode apertures and biased between the headset and the subject's head by the associated biasing flap. A plurality of electrode covers constructed at least partially of flexible, liquid-absorbing material are arranged and adapted to be electrically-conductive, receive EEG signals from the subject's head and transmit such signals to at least one the EEG signal transmission wire of the headset during use of the headset. Each electrode cover at least partially encapsulates an electrode and is laden with electrically-conductive liquid during use of the headset. Each biasing flap is configured to bias the associated electrode cover into contact with the subject's head to allow the associated cover to receive EEG signals from the subject's head.

In at least one embodiment, a method of using the immediately above-referenced apparatus includes releasably suspending the plurality of electrodes along with their associated electrically-conductive, liquid laden, electrode covers within the respective associated electrode apertures in the headset. The headset is placed on the subject's head. At least some of the biasing flaps bias their associated electrodes in the direction of the subject's head independent of the other electrodes in the headset. At least some of the electrode covers receive useful signals from the subject's head and transmit the received signals to at least one EEG signal transmission wire in the headset.

In some embodiments, the present disclosure involves apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset further includes a plurality of electrode stations and a plurality of intermediate portions extending between the electrode stations and shaped and sized to form open spaces therebetween. Each electrode station includes an electrode aperture extending therethrough from the outer side to the inner side of the headset. The headset further includes a plurality of biasing flaps and at least first and second flap fasteners associated with each biasing flap. Each biasing flap is coupled to the-headset and at least partially aligned over one of the electrode apertures. The flap fasteners are adapted to secure the associated biasing flap to the headset on opposite sides of the associated electrode aperture. The headset further includes at least one EEG signal transmission wire associated with the electrode stations for receiving EEG signals.

In these embodiments, a plurality of removable electrodes are releasably engageable with the headset and useful to facilitate the transmission of EEG signals from the subject's head to at least one the EEG signal transmission wire of the headset during use of the headset. Each electrode includes a top end, bottom end and at least one side extending therebetween. Each electrode is configured to be releasably suspended within one of the electrode apertures and biased between the headset and the subject's head by the associated biasing flap. A plurality of electrode covers constructed at least partially of flexible, liquid-absorbing material is arranged and adapted to be electrically- conductive, receive EEG signals from the subject's head and transmit such signals to at least one the EEG signal transmission wire of the headset during use of the headset. Each electrode cover at least partially encapsulates an electrode and is laden with electrically-conductive liquid during use of the headset. Each biasing flap is configured to bias the associated electrode cover into contact with the subject's head to allow the associated cover to receive EEG signals from the subject's head.

In at least one embodiment, a method of using the immediately above-referenced apparatus includes releasably suspending the plurality of electrodes along with their associated electrically-conductive, liquid laden, electrode covers within the respective associated electrode apertures in the headset. The headset is placed on the subject's head. At least some of the biasing flaps bias their associated electrodes in the direction of the subject's head independent of the other electrodes in the headset. At least some of the electrode covers receive useful signals from the subject's head and transmit the received signals to at least one EEG signal transmission wire in the headset.

In certain embodiments, the present disclosure involves apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset also includes a plurality of electrode stations and a plurality of intermediate portions extending between the electrode stations and shaped and sized to form open spaces therebetween. Each electrode station includes an electrode aperture extending therethrough from the outer side to the inner side of the headset. The headset further includes a plurality of biasing flaps, each biasing flap being directly coupled to the headset and at least partially aligned over one of the electrode apertures. The headset further includes at least one EEG signal transmission wire associated with the electrode stations for receiving EEG signals.

In these embodiments, a plurality of removable electrodes is releasably engageable with the headset and useful to facilitate the transmission of EEG signals from the subject's head to at least one the EEG signal transmission wire of the headset during use of the headset. Each electrode includes a top end, bottom end, at least one side extending therebetween and at least one protrusion extending outwardly from at least one side. Each protrusion is arranged and adapted to selectively position the associated electrode relative to the associated electrode aperture. Each electrode is configured to be releasably suspended within one of the electrode apertures and biased towards the subject's head by the associated biasing flap.

In at least one embodiment, a method of using the immediately above-referenced apparatus includes releasably suspending the plurality of electrodes within the respective associated electrode apertures in the headset and placing the headset on the subject's head. At least some of the biasing flaps bias their associated electrodes in the direction of the subject's head independent of the other electrodes in the headset.

The present disclosure also includes embodiments involving apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset also includes a plurality of electrode stations and a plurality of intermediate portions extending between the electrode stations and shaped and sized to form open spaces therebetween. Each electrode station includes an electrode aperture extending therethrough from the outer side to the inner side of the headset. The headset further includes a plurality of biasing flaps and at least first and second flap fasteners associated with each biasing flap. Each biasing flap is coupled to the headset and at least partially aligned over one of the electrode apertures. The flap fasteners are adapted to secure the associated biasing flap to the headset on opposite sides of the associated electrode aperture. The headset further includes at least one EEG signal transmission wire associated with the electrode stations for receiving EEG signals.

In these embodiments, a plurality of removable electrodes are releasably engageable with the headset and useful to facilitate the transmission of EEG signals from the subject's head to at least one the EEG signal transmission wire of the headset during use of the headset. Each electrode includes a top end, bottom end, at least one side extending therebetween and at least one protrusion extending outwardly from at least one side. The protrusion is arranged and adapted to selectively position the associated electrode relative to the associated electrode aperture. Each electrode is configured to be releasably suspended within one of the electrode apertures and biased towards the subject's head by the associated biasing flap.

In at least one embodiment, a method of using the immediately above-referenced apparatus includes releasably suspending the plurality of electrodes within the respective associated electrode apertures in the headset and placing the headset on the subject's head. At least some of the biasing flaps bias their associated electrodes in the direction of the subject's head independent of the other electrodes in the headset.

Accordingly, the present disclosure includes features and advantages which are believed to enable it to advance the art of brain signal recovery technology. Characteristics and advantages of the present disclosure described above and additional features and benefits will be readily apparent to those skilled in the art upon consideration of the following detailed description of various embodiments, the accompanying drawings and appended claims.

BRIEF DESCRIPTION OF THE DRAWINGS

The following figures are part of the present specification, included to demonstrate certain aspects of various embodiments of this disclosure and referenced in the detailed description herein:

FIG. 17 is a top partially-disassembled view of the exemplary headset system shown in FIG. 12;

DETAILED DESCRIPTION OF PRESENTLY PREFERRED EMBODIMENTS

Figure 1:
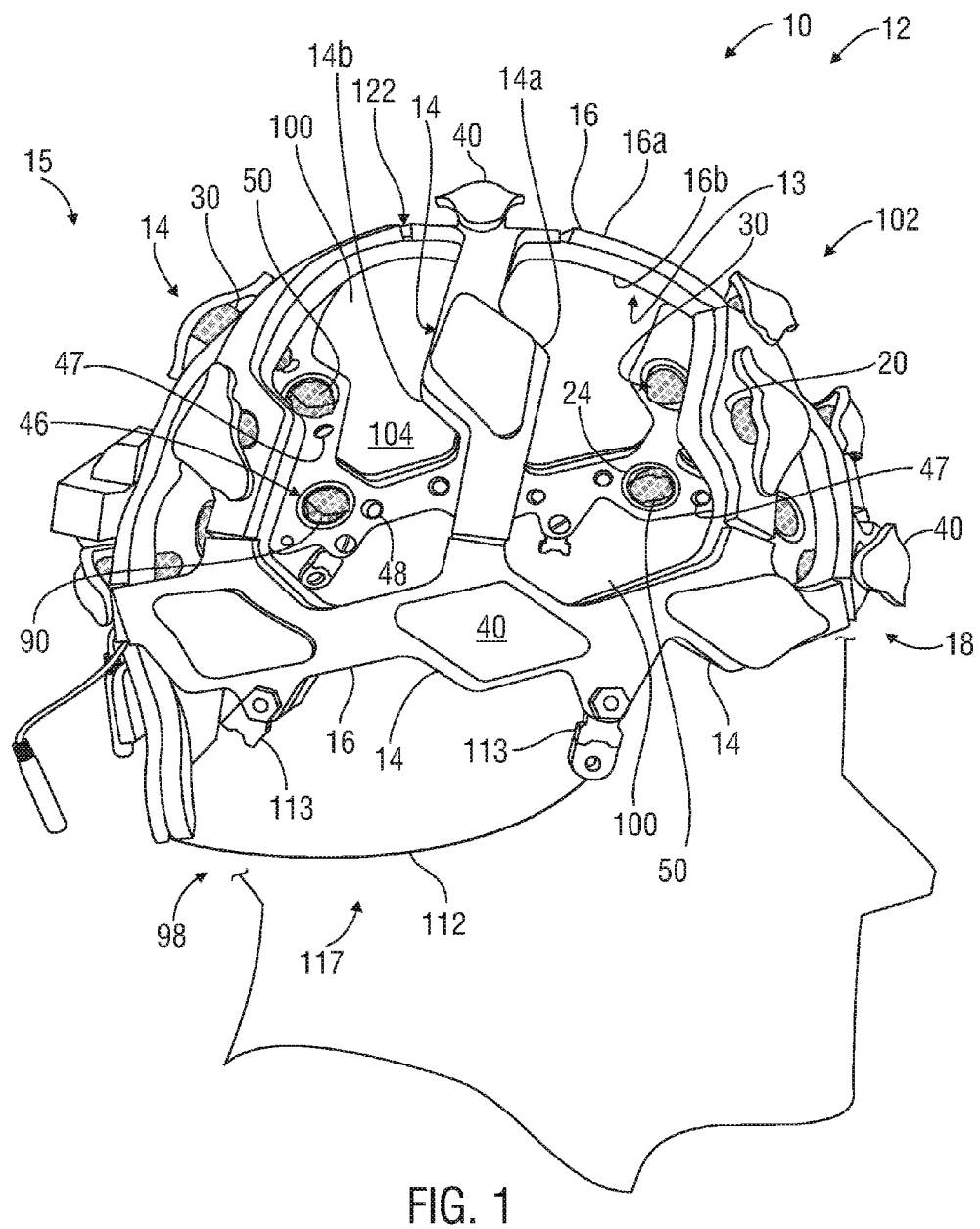
FIG. 1 is a side view of an exemplary signal receiving headset system shown as it would be positioned on a human subject's head in accordance with an embodiment of the present disclosure.

Characteristics and advantages of the present disclosure and additional features and benefits will be readily apparent to those skilled in the art upon consideration of the following detailed description of exemplary embodiments of the present disclosure and referring to the accompanying figures. It should be understood that the description herein and appended drawings, being of example embodiments, are not intended to limit the claims of this patent application or any patent or patent application claiming priority hereto. On the contrary, the intention is to cover all modifications, equivalents and alternatives falling within the spirit and scope of the claims. Many changes may be made to the particular embodiments and details disclosed herein without departing from such spirit and scope.

In showing and describing preferred embodiments in the appended figures, common or similar elements are referenced with like or identical reference numerals or are apparent from the figures and/or the description herein. When multiple figures refer to a component or feature with the same reference numeral, any description herein of the component or feature with respect to any of the figures applies equally to the other figures to the extent such description does not conflict with a description herein of the other figure(s). The embodiments shown in the figures are illustrated for simplicity and clarity and have not necessarily been drawn to scale. Also, common but well-understood components useful or necessary in the illustrated embodiments may not be depicted in the appended figures in order to facilitate a less obstructed view of other depicted features. Certain features and certain views of the figures may be shown exaggerated in scale or in schematic in the interest of clarity and conciseness.

As used herein and throughout various portions (and headings) of this patent application, the terms "invention", "present invention" and variations thereof are not intended to mean every possible embodiment encompassed by this disclosure or any particular claim(s). Thus, the subject matter of each such reference should not be considered as necessary for, or part of, every embodiment hereof, or of any particular claim(s) merely because of such reference. The terms "coupled", "connected", "engaged" and the like, and variations thereof, as used herein and in the appended claims are intended to mean either an indirect or direct connection or engagement. Thus, if a first device couples to a second device, that connection may be through a direct connection, or through an indirect connection via one or more other devices and/or connections.

Certain terms are used herein and in the appended claims to refer to particular components. As one skilled in the art will appreciate, different persons may refer to a component by different names. The use of a particular or known term of art as the name of a component herein is not intended to limit that component to only the known or defined meaning of such term (e.g. nut). Further, this document does not intend to distinguish between components that differ in name but not function. Also, the terms "including" and "comprising" are used herein and in the appended claims in an open-ended fashion, and thus should be interpreted to mean "including, but not limited to . . . ." Further, reference herein and in the appended claims to components and aspects in a singular tense does not necessarily limit the present disclosure or appended claims to only one such component or aspect, but should be interpreted generally to mean one or more, as may be suitable and desirable in each particular instance.

As used herein, the terms "substantially", "generally" and variations thereof means and includes (i) completely, or 100%, of the referenced parameter, variable or value and (ii) a range of values less than 100% based upon the typical, normal or expected degree of variation or error for the referenced parameter, variable or value in the context of the particular embodiment or use thereof, such as, for example, 90-100%, 95-100% or 98-100%. However, in some instances of the use of the terms "generally", "substantially" and variations thereof herein, the above definition may not apply, as should be apparent from the context of such use. It is also to be noted that the terms "comprising," "including," and "having" may be used interchangeably.

The following description is not to be taken in a limiting sense, but is made merely for the purpose of describing the general principles of exemplary embodiments; many additional embodiments of this disclosure are possible. The described features, structures, characteristics and other details of the present disclosure may be combined in any suitable manner in one or more embodiments. One skilled in the relevant art will recognize that the embodiments of the present disclosure may be practiced with our without one or more of the exemplary details provided herein, or with other methods, components, materials, and so forth.

Further, all numbers expressing dimensions, physical characteristics and so forth used in the specification and claims are to be understood as being modified in all instances by the term "about". Accordingly, unless explicitly indicated to the contrary, the numerical values set forth in the following specification and claims may vary depending upon the desired properties sought to be obtained by the practice of one or more embodiments of the disclosure. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.3, or 5.5 to 10, or 2.7 to 6.1.

For the purposes of promoting an understanding of the principles of the present disclosure, reference will now be made to the embodiments illustrated in the drawings.

Figure 2:
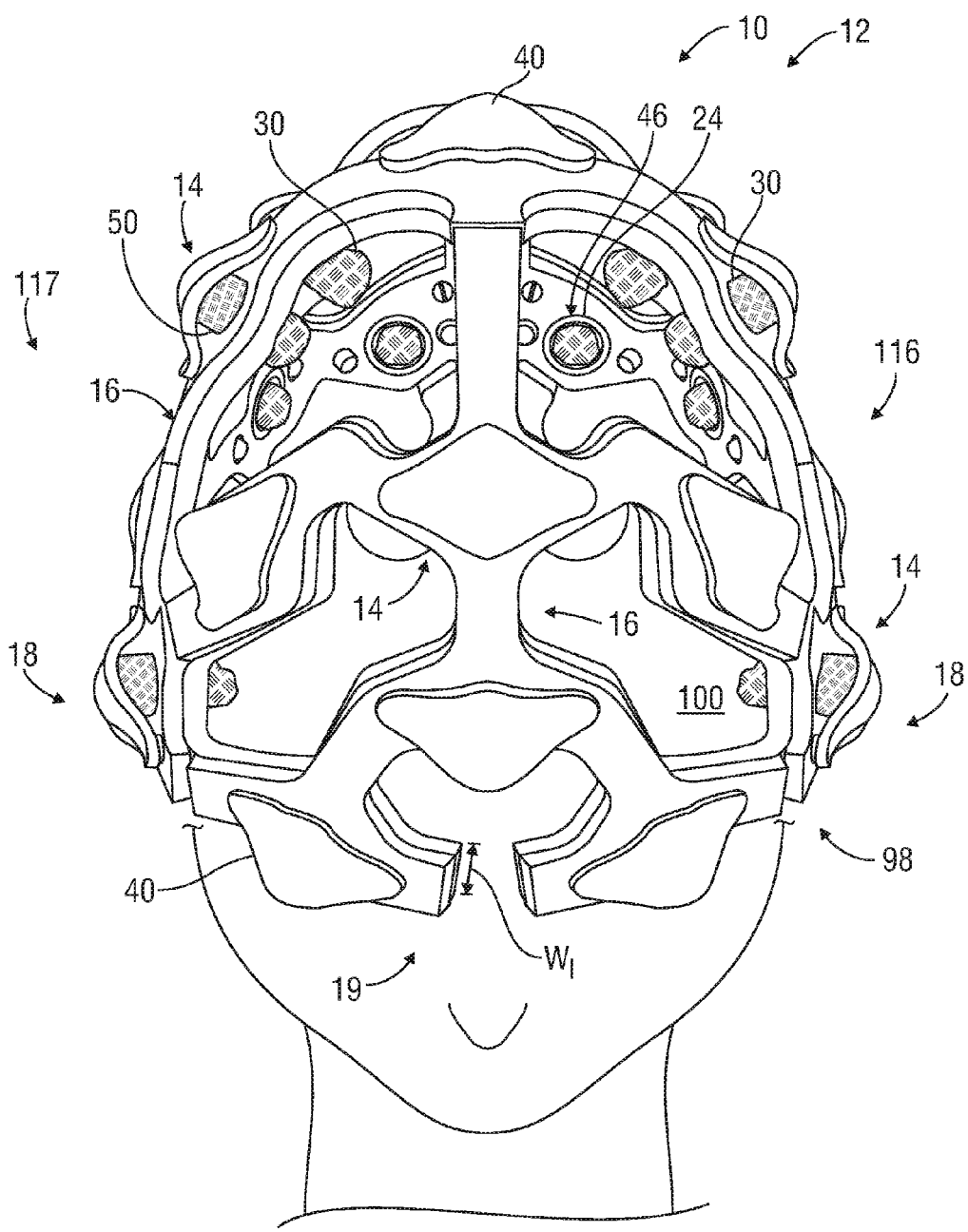
FIG. 2 is a front view of the exemplary headset system shown in FIG. 1.
Figure 3:
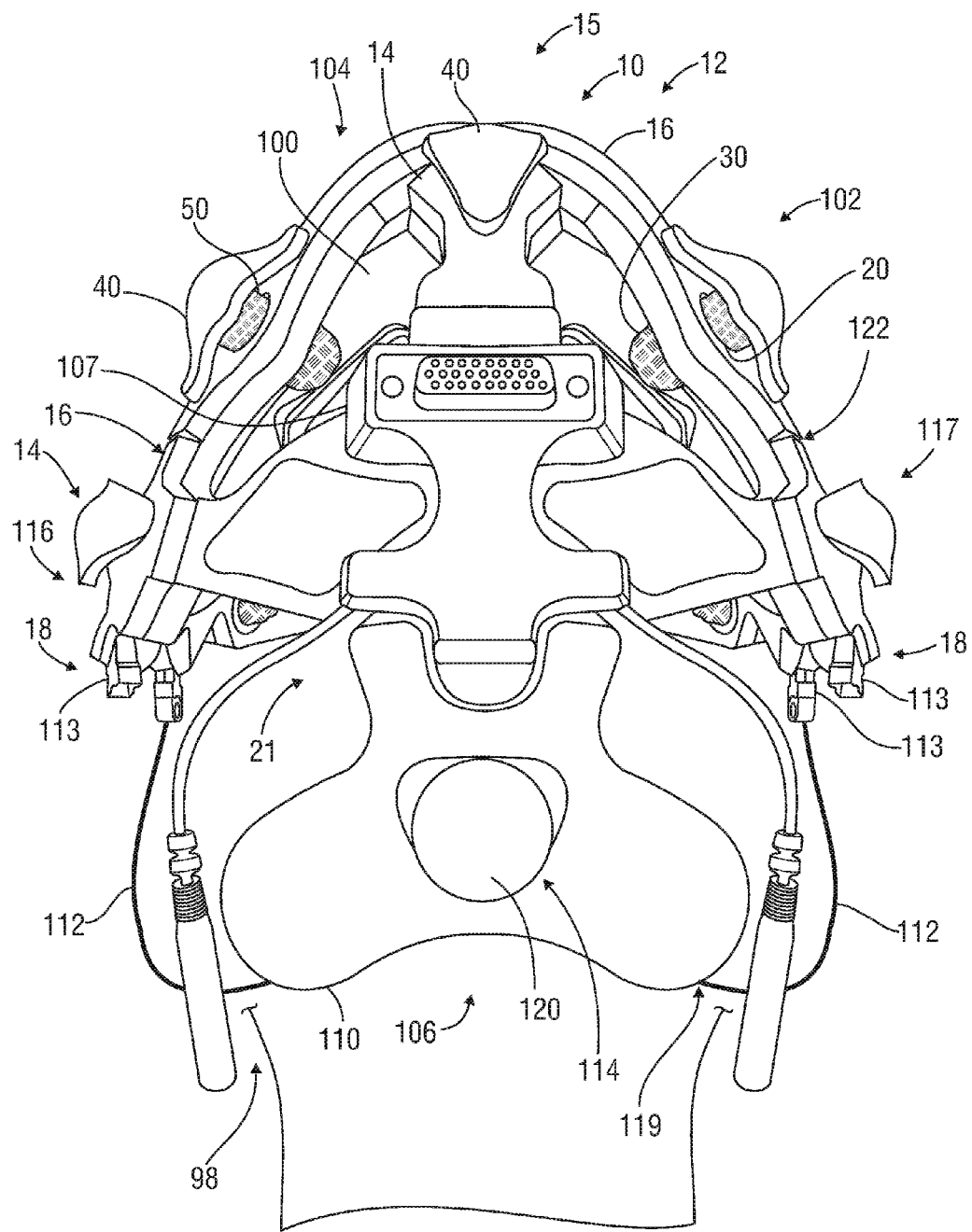
FIG. 3 is a rear view of the exemplary headset system shown in FIG. 1.

Referring initially to FIGS. 1-3, in an independent aspect of the present disclosure, an embodiment of a removable, re-suable signal receiving headset system 10 for receiving EEG signals (or other signals) from a human subject is shown. The exemplary system 10 includes a headset, or cap, 12 that is releasably securable at least partially around the subject's head 98 over at least part of the subject's scalp 102. As used herein, the terms "head", "cranium" and the like are used interchangeably. The exemplary headset 12 has an inner side 13 closest to the subject's scalp 102 when the headset 12 is positioned on the subject's head 98 and an outer side 15 that faces away from the scalp 102.

The cap 12 may have any suitable form, construction, configuration, components and operation. In this example, the cap 12 is a "webbed" cap and includes a plurality of electrode stations 14 and a plurality of intermediate portions, or strips, 16, for capping the area 104 of the subject's scalp 102 to be tested or measured (the "scalp test area" 104). The exemplary electrode stations 14 are associated with at least one signal transmission wire, or wire lead 70 (e.g. FIG. 4) carried by the cap 12. Each illustrated electrode station 14 includes an electrode aperture 20 and an electrode biasing flap 40. Each exemplary electrode aperture 20 extends through the headset 12 from the outer side 15 to the inner side 13 thereof and is configured to suspend or carry a removable electrode 30 useful for facilitating the transmission of signals (e.g. EEG signals) from the subject's brain to one or more of the signal transmission wires 70. Typically, for EEG testing, the electrode apertures 20 are positioned at predetermined locations in the cap 12 for positioning the electrodes 30 at specific locations relative to the subject's brain. The illustrated biasing flap 40 is coupled to the outer side 15 of the headset 12, at least partially aligned over the associated electrode aperture 20 and configured to abut, or grip, and bias the associated electrode 30 in the direction of the subject's head 98.

The illustrated intermediate portions 16 generally extend between the electrode stations 14. While the portions 16 are also referred to herein as "strips" and may, in some instances, be elongated in shape, the portions 16 need not each take the shape of an elongated strip. Thus, as used herein, the terms "strip", "intermediate portion" and variations thereof generally means a section of the cap 12 disposed between, or adjacent to, one or more stations 14.

Figure 4:
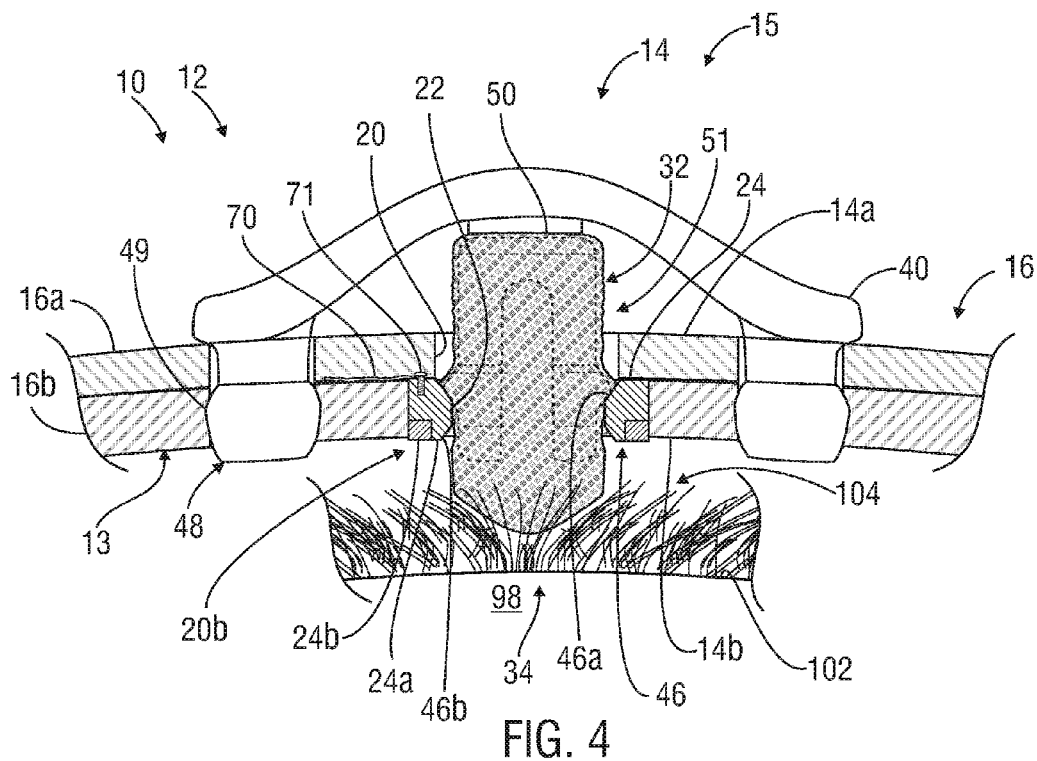
FIG. 4 is a partial cross-sectional view of part of the exemplary headset system of FIG. 1 showing an exemplary electrode is an exemplary retracted position relative to the illustrated exemplary electrode aperture.
Figure 5:
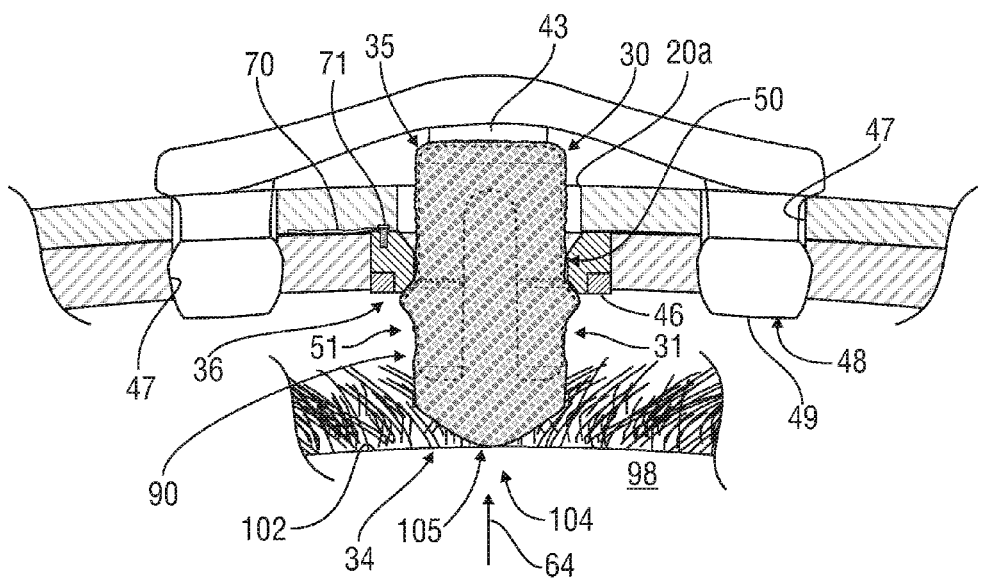
FIG. 5 is a partial cross-sectional view of part of the exemplary headset system of FIG. 1 showing the exemplary electrode of FIG. 4 in an exemplary extended position relative the illustrated exemplary electrode aperture.

Referring now to FIGS. 4-5, one of the exemplary electrodes 30 is configured to be releasably suspended in each electrode aperture 20 during use of the system 10. In this embodiment, the electrodes 30 are not glued or bonded to the headset 12. Each illustrated electrode 30 includes a top end 35, a bottom end 34, at least one side 31 extending therebetween and at least one outer side surface 32 extending at least partially along the side 31(s). The exemplary electrode 30 is configured to be biased between the headset 12 and the subject's head 98 by its associated biasing flap 30. The electrode 30 and/or one or more components related thereto are configured to receive signals (e.g. EEG signals) from the subject's brain and transmit such signals to at least one of the wire leads 70 of the headset 12.

In this embodiment, each electrode 30 is at least partially encapsulated by an electrode sock, or cover, 50 constructed at least partially of flexible, electrically-conductive liquid absorbing material. During use of the illustrated headset 12, each cover 50 is adapted to be laden with electrically-conductive liquid 90, electrically-conductive, at least partially sandwiched (by its associated biasing flap 40) between its associated electrode 30 and the subject's head 98 into contact with the subject's scalp test area 104 to receive signals (e.g. EEG signals) from the subject's head 98 and transmit them to at least one wire lead 70 of the headset 12. As used herein, the terms "laden" and variations thereof means sufficiently covered, soaked, saturated or near-saturated with one or more electrode wetting agents to allow the laden component to receive useful signals from the subject's brain through the head 98 and scalp 102 thereof. A useful signal is one that may be meaningfully used in the desired test/analysis (e.g. EEG measurement testing/analysis). As used herein, the terms "electrically-conductive liquid" and variations thereof mean and refer to liquids, gels and other suitable chemical combinations or formulations having properties that allow a component laden therewith to receive useful signals from the subject's head 98 and scalp 102. For example, each cover 50 may include a bottom end 52 that is electrically conductive to an exterior side surface 51 thereof. The exemplary bottom end 52 is configured to electrically-conductively engage the subject's head 98 to receive EEG signals therefrom, and the side surface 51 electrically conducts the received signals to one or more wire leads 70 in the headset 12.

In various embodiments, the electrodes 30 and/or covers 50 may be reusable, disposable or both. In some embodiments, the electrode covers 50 may not be included.

Referring back to FIGS. 1-3, the headset 12 and its related components may be constructed of any suitable material or combination of materials. For example, the cap 12 (e.g. electrode stations 14 and strips 16) and/or its related components or the outer layers thereof, may be constructed at least partially of one or more non-absorbent, water-resistant or water-proof materials (e.g. closed-cell foam) and/or easy-to-clean material. If desired, the cap 12 may be constructed of material that includes antimicrobial and/or biostatic agents. For example, depending upon the particular scenario, the stations 14 and strips 16 may be constructed of plastic, rubber, foam, Croslite™, silicon, Trileon™, any other type of EVA or a combination thereof. Croslite™ is a proprietary closed-cell, anti-microbial, resin material developed for Crocs™, Inc. Trileon™ is a closed-cell copolymer developed by Scott Seamans for SoftScience™, Inc. Such construction of the cap 12 and related components may be useful, for example, to avoid the transfer of sweat, dirt, germs, microbes and/or bacteria from one or more subject's head 98 to the cap 12 during use of the headset system 10 and/or to avoid problems caused thereby. For another example, such construction of the cap 12 and related components may render them re-usable on multiple subjects with minimal or no cleaning, to meet sanitary standards or requirements, and/or any other desired purpose(s).

Still referring to FIGS. 1-3, the electrode stations 14 and strips 16 may have any suitable form, configuration, construction and operation. For example, the electrode stations 14 may be integrally formed with the strips 16. In the illustrated embodiment, the electrode stations 14 are shown integral to the strips 16, have an overall generally diamond-shape and an average width that is greater than the average width of the exemplary strips 16. In other embodiments, the stations 14 may have an overall generally round, oval, rectangular, square or any other shape. In some embodiments, the stations 14 and strips 16 may be separate components that are interconnected in any suitable manner, such as with fasteners, adhesive or a combination thereof.

If desired, the strips 16 and/or stations 14 may be constructed of a material or combination of materials that is semi-rigid, conformable, resilient, elastic or a combination thereof. Also if desired, the strips 16 and/or stations 14 may be constructed and shaped to provide a desired mix of compressive, elastic, bending, flexing and conforming properties. For example, the width of the strips 16 may be selected to assist in providing the desired flexibility thereof. In the embodiment of FIGS. 1-5, the average width $W_1$ (FIG. 2) of each illustrated strip 16 ranges from approximately ¼ inch-approximately ¾ inch, and is preferably approximately ½ inch. However, the illustrated strips 16 may have any other desired width.

For another example, some or all of the electrode stations 14 and/or strips 16 may be formed of multiple layers. In this embodiment, the stations 14 and strips 16 are each formed of two layers, the electrode stations 14 having upper and lower layers 14a, 14b and the strips 16 including upper and lower layers 16a, 16b. Multiple layers may be included for any suitable purpose. For example, multiple layers of stations 14 and/or strips 16 may provide the desired combination of stiffness and flexibility of the stations 14 and/or strips 16. In this embodiment, two layers of flexible Croslite™, Trileon™ or other antimicrobial material for the stations 14 and/or strips 16 may provide the desired combination of stiffness and flexibility of the headset 12. For another example, multiple layers may provide the desired protection of internally disposed components of the headset 12, such as the wire leads 70.

Figure 6:
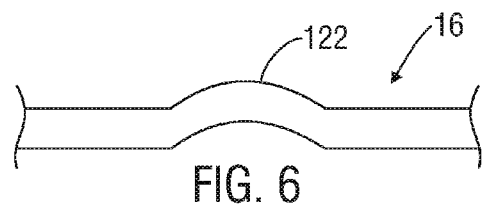
FIG. 6 is a partial side view of an exemplary intermediate portion of an embodiment of a headset system having a fold-type flex point in accordance with an embodiment of the present disclosure.
Figure 7A:
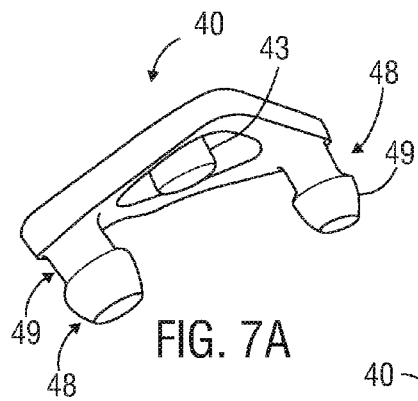
FIG. 7A is a perspective view of an exemplary electrode biasing flap useful in the exemplary headset system shown in FIG. 1 in accordance with an embodiment of the present disclosure.
Figure 7B:
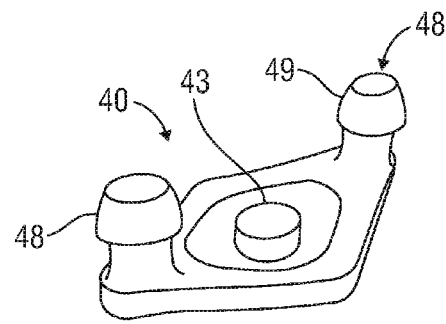
FIG. 7B is another perspective view of the exemplary electrode biasing flap shown in FIG. 7A.
Figure 7C:
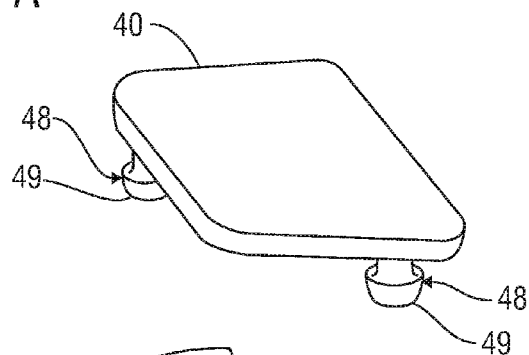
FIG. 7C is yet another perspective view of the exemplary electrode biasing flap shown in FIG. 7A.
Figure 8:
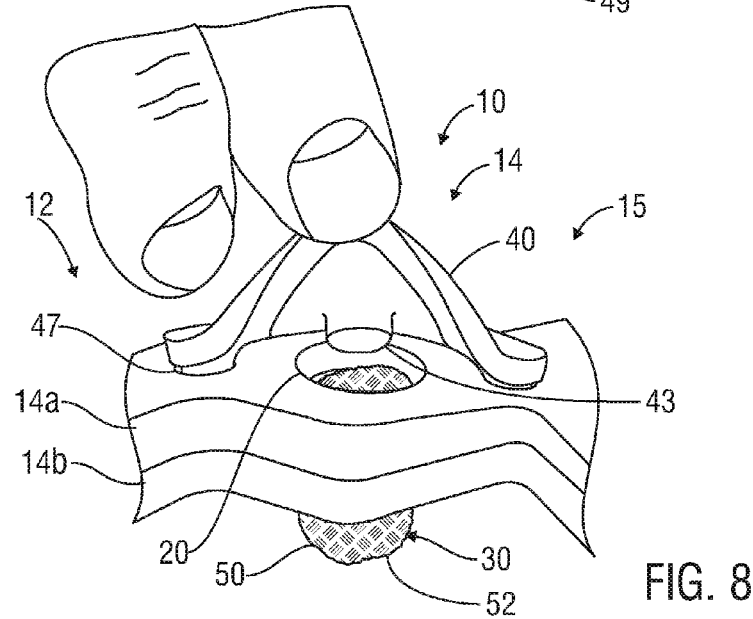
FIG. 8 is a side view of part of the part of the exemplary headset system of FIG. 1 showing an exemplary electrode biasing flap being manually stretched upwardly to show the underside thereof.

In many embodiments, some or all of the strips 16 may be constructed and configured to enhance the flexibility of the strips 16 and headset 12, allow the strips 16 to be compressed or conform to the shape of the subject's head 98 or a combination thereof. For example, one or more of the strips 16 may include one or more flex points 122 formed or provided therein. In the illustrated example, each flex point 122 is a break in the outer layer 16b of some of the strips 16. In other embodiments, such as shown in FIG. 6, the illustrated flex point 122 is a bend or fold in the strip 16. Depending upon the configuration, the exemplary flex point(s) 122 may, for example, allow the strips 16 to displace upwardly or downwardly, such as when one end of the strip(s) 16, or headset 12, is squeezed or pushed towards its other end, avoiding twisting, bulging or buckling and/or assisting in preserving the conformance of the cap 12 to the subject's head 98.

Figure 18:
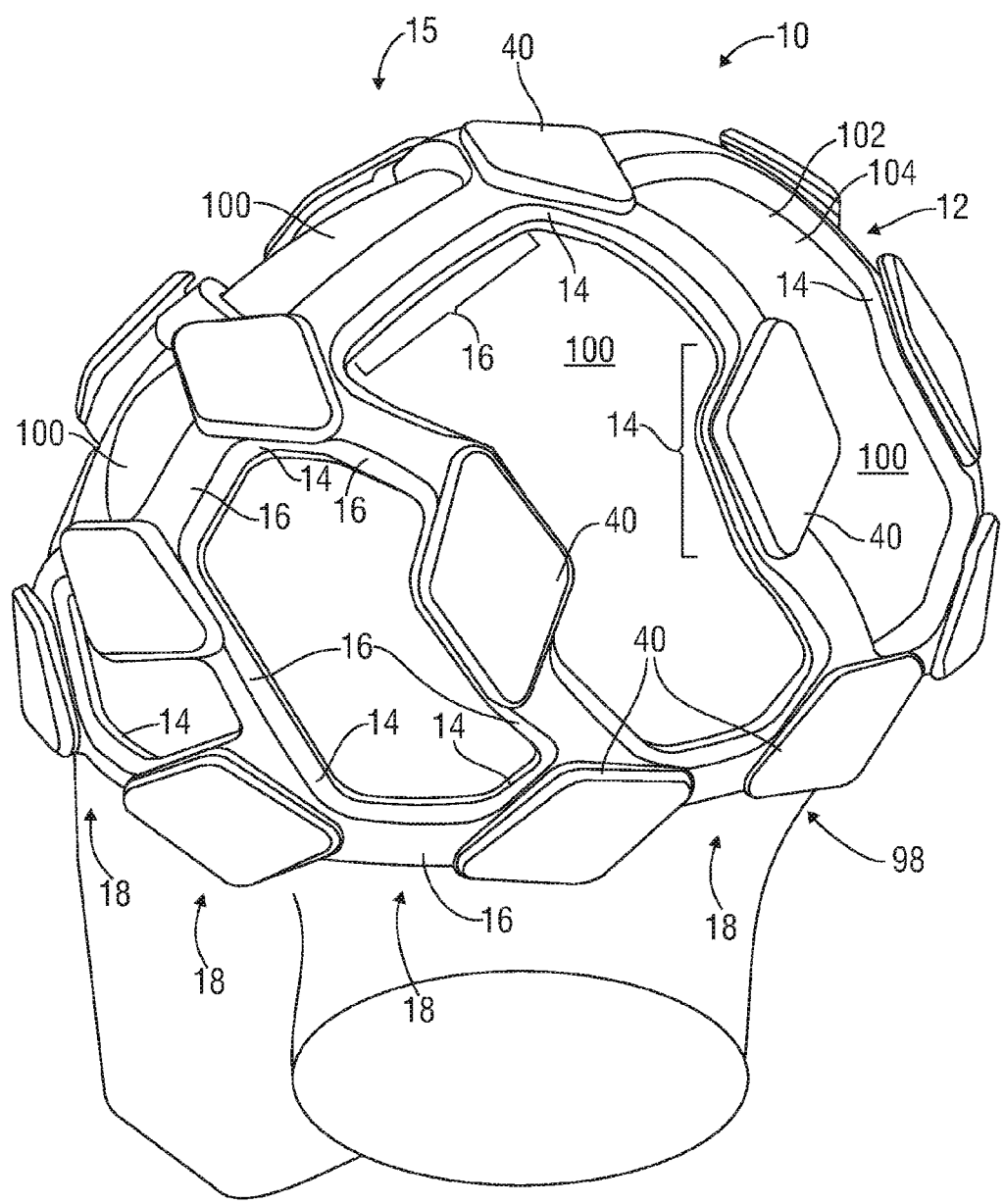
FIG. 18 is a perspective view of an exemplary signal receiving headset system shown positioned on a human subject's head in accordance with another embodiment of the present disclosure.

Still referring to FIGS. 1-3, the electrode biasing flaps 40 may have any suitable form, configuration and operation. For example, the flaps 40 may be constructed at least partially of rubber, foam, foam rubber, a rubbery material, closed-cell foam, Croslite™, impact-absorbing elastic, or any other material suitable for flexing and returning to its original position, resiliently biasing the electrode 30 downwards toward the scalp 102 as desired and is otherwise suitable for use as part of the system 10. The flaps 40 may be positioned to partially, or entirely, cover, or align over, the respective electrode apertures 20 of their associated electrode stations 14. In this embodiment, each flap 40 is unperforated, or solid, above its associated electrode aperture 20 and aligns generally entirely over the aperture 20 (see also, FIG. 18). If desired, the flap 40 may include at least one nipple 43 (e.g. FIGS. 7A-C and FIG. 8) configured to abut and apply biasing forces to the top end 35 of an electrode 30.

In other embodiments, such as shown in FIGS. 12-15, the flap 40 may align over only part of the associated electrode aperture 20. In this example, the solid part of the exemplary flap 40 aligns over only the upper edge 20a of the aperture 20 because the flap 40 includes a flap hole 42. The flap hole 42 may have any suitable form, construction and configuration. In this embodiment, the flap hole 42 aligns over the electrode aperture 20 of the associated electrode station 14 and is configured to also suspend or carry the associated electrode 30. The flap hole 42 may also have any desired operation. For example, the flap hole 42 may be large enough to allow the passage of an electrode 30 therethrough and/or configured to assist in the positioning of the electrode 30 (e.g. FIGS. 16A-C), such as will be described further below.

Referring again to FIGS. 4-5, the flaps 40 may be engaged with the headset 12 in any suitable manner. For example, each flap 40 may be releasably or permanently fastened to an electrode station 14 and/or one or more strips 16 with flap fasteners 48. The flap fasteners 48 may have any suitable form, configuration, construction and operation. In this embodiment, the flap fasteners 48 are barbed, or arrow-shaped, extensions 49 integrally formed in the flap 40 on opposing sides, or corners, thereof (see also, FIGS. 7A-C). For connection with the cap 12, each illustrated extension 49 releasably extends into and engages a barb-receiving hole 47 formed in an electrode station 14 or strip 16 (see also, FIG. 8). In this embodiment, the barb-receiving holes 47 extend through both layers 14a, 14b of the associated station 14 (or layers 16a, 16b of the associated strip 16), such as to ensure a secure fit during stretching, biasing and other movement (e.g. twisting) of the flaps 40 when the headset 12 is in use. Further, the exemplary fasteners 48 are removable from the headset 12. In other embodiments, the flap fasteners 48 may instead be permanently fixed to the headset 12.

In the embodiment of FIGS. 13 and 16A-C, the flap fasteners 48 are removable threaded plastic bolts 56 secured upwardly into receiving nuts 53. The electrode-biasing flaps 40 may instead, or also, be secured to the headset 12 using one or more adhesives. It should be noted that, in some embodiments, the headset 12 may include one or more springs or other forms of elastic elements used in combination with or instead of the flaps 40 for biasing the electrodes 30 downwardly into contact with the subject's head 98.

In another independent aspect of the present disclosure, referring back to FIGS. 4-5, the electrodes 30 may be inserted and removed from the headset 12 in any suitable manner. In some embodiments, the electrodes 30 are configured to be moveable into and out of the electrode apertures 20 in both directions. In the present embodiment, since the electrode biasing flap 40 is solid above the aperture 20, insertion or removal of the electrode 30 from the top, or outer side 15, of the headset 12 would require disengaging at least one of the flap fasteners 48 of each flap 40 to move the flap 40 away from the electrode aperture 20. Thus, the easier and quicker technique for inserting and remove the electrodes 30 in this embodiment is to insert the electrode 30 up into the electrode aperture 20 from below (from the inner side 13 of the headset 12) and remove it back down through the aperture 20 (in the direction of the inner side 13 of the headset 12). Similarly, in the embodiment of FIGS. 19A-C, the electrode 30 is inserted upwardly (arrows 58) into the aperture 20 and can be later removed downwardly in the reverse direction.

In the embodiment of FIGS. 13-16C, the illustrated electrodes 30 are also moveable in both directions into and out of the headset 12 because the flaps 40 each include a flap hole 42 through which the electrode 30 may pass. However, in this particular arrangement, the electrodes 30 are preferably insertable into the headset 12 from the top, or outer side 15, of the headset 12 (arrows 60, FIGS. 16A-B) and removed in the same direction (toward the inner side 13 of the headset 12). The electrodes 30 of this embodiment are thus preferably moveable in one direction only.

Referring back to FIGS. 1-3, in another independent aspect of the present disclosure, in some embodiments, the exemplary headset 12 may include one or more base sections, or cap rims, 18 that at least partially aligns over and around a lower area of the subject's head 98. The cap rim 18 may have any desired form, components and construction and may be configured for any desired purpose. For example, the cap rim 18 may be configured to provide tension to assist in the placement and/or positioning of the electrodes 30 relative to the scalp test area 104.

If desired, the cap rim 18 may include some of the electrode stations 14 interconnected by intermediate sections 16. In some embodiments, the cap rim 18 at the front end 19 of the headset 12 (e.g. FIG. 2) may be open. In this example, the intermediate sections 16 at the front end 19 along the cap rim 18 of the headset 12 are not connected, such as to provide the desired flexibility of the headset 12, assist in achieving a good fit to the subject's head 98, and/or other suitable purpose. In various embodiments, the cap rim 18 at the rear end 21 or either side 116, 117 of the headset 12, or a combination, thereof may be open (not shown). If the cap rim 18 is open at any location, one or more releasable connectors, such as a pair of mateable velcro straps, or snap connectors, may be included to adjustable connect the adjacent open sections of the rim 18, such as to assist in securing the headset 12 to the subject's head 98.

In some embodiments, the cap 12 may be adjustably tightened around the circumference of the subject's head 98 and/or along one or more sides thereof to achieve a desired fit or for any other desired purpose. The cap 12 may be adjustably tightened in any suitable manner. For example, the cap 12 may be adjustably tightened around the cap rim 18. Referring specifically to FIG. 3, in this embodiment, the cap 12 is configured with a closure mechanism, or tightener, 114 useful to assist in tensioning or positioning the headset 12 as desired on the subject's head 98, moving the headset 12 down and around the head, adequately positioning the electrodes 30 (e.g. FIGS. 4-5) as desired (e.g. approximately perpendicular) relative to the scalp test area 104 without the need for a chinstrap, any other suitable purpose or a combination thereof.

The tightener 114 may have any suitable form, configuration, components and operation. For example, may one or more wires, or cables, 112 extending from each side 116, 117 of the headset 12, or along the rim 18, may be selectively tightened and/or loosened. In the illustrated example, the tightener 114 includes a ratcheting spool 120 mounted on a platform 110 and upon which a cable 112 coupled to each side 116, 117 is wound. If desired, the platform 110 may be positioned proximate to the occipital area 106 of the subject's head 98, such as for support and comfort. The exemplary ratcheting spool 120 is rotated to draw in and tension the cable 112 and draw the headset sides 116, 117 toward the rear. If desired, the ratcheting spool 120 may be configured to also loosen the cable(s) 112. The ratcheting spool 120 may constructed of any suitable material, such as plastic. For example, the ratcheting spool 120 may be a commercially available spool commonly used in sports equipment.

Figures 20A, 20B:
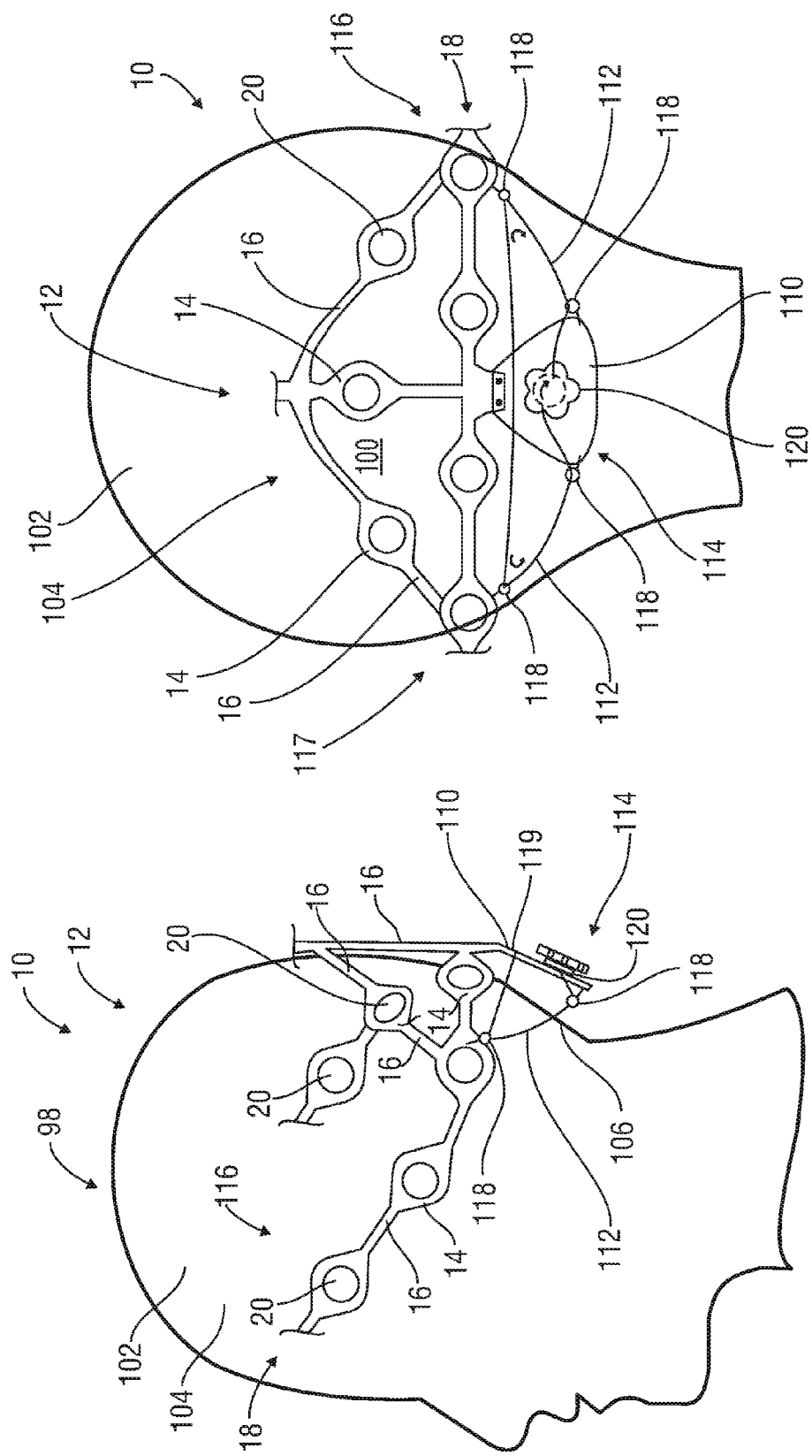
FIG. 20A is a side view of a portion of the exemplary headset system shown in FIG. 12 showing an exemplary tightener in accordance with an embodiment of the present disclosure.
FIG. 20B is a rear view of a portion of the exemplary headset shown in FIG. 20A.

Still referring to the embodiment of FIG. 3, if desired, the cables 112 may be selectively connectable to the headset 12 at different positions to achieve the desired effect. In this embodiment, each cable 12 may be snap fit into one among multiple receivers 113 disposed at different positions along the cap rim 18. In some embodiments, one or more cable channels 119 may be formed in the platform 110. Further, if desired, the cables 112 may extend through one or more guides, or pulleys, 118 (e.g. FIGS. 20A-B). In various embodiments, the cable(s) 112 may be connected to a chin strap and/or comprise complementary Velcro® straps fastenable to each other. Further alternate embodiments may include a helmet strap attached to each side 116, 117 of the headset 12 and releasably fastened by mating connectors. In yet other embodiments, a tightener 114 may not be included.

Referring back to FIGS. 1-3, in another independent aspect of the present disclosure, the exemplary cap 12 may have a "webbed" configuration, or arrangement, to form open spaces between some or all of its structural members (e.g. stations 14, strips 16, etc.) for any suitable purpose. For example, the strips 16 (and stations 14) may form one or more web open areas 100 to allow for visual inspection of the scalp test area 104, the position of each electrode 30 relative to the head 98 and/or the contact interface 105 (e.g. FIGS. 4-5) therebetween, to determine if the electrode 30 (or related component(s)) is making sufficient contact with the scalp test area 104 to receive useful signals from the subject's brain, any other suitable purpose or a combination thereof. As used herein, the terms "contact interface" and variations thereof means and refers to the point or area of contact between an electrode 30 or one or more components related thereto (e.g. electrode cover 50) and the scalp 102 where the electrode 30 (or related component(s)) receives signals from the subject's brain. In this illustrated embodiments (e.g. FIGS. 4-5), the exterior side surface 51 of each electrode cover 50 and each contact interface 105 are visible through the open areas 100.

For another example, the web open area 100 may assist in allowing the portions 16 of the headset 12 to bend, conform, stretch, compress, and/or fold without buckling or bulging, such as when the cap 12 is tightened or tensioned around the subject's head 98. Such flexibility of the cap 12 may, in at least some instances, allow the exemplary electrode stations 14 to be positioned substantially parallel to the scalp test area 104 and/or the electrodes 30 to be positioned substantially perpendicularly to the scalp test area 104 (e.g. FIGS. 4-5).

The web open area(s) 100 may have any suitable size, configuration and orientation. In some embodiments, for example, the web open areas 100 of the cap 12 may occupy at least approximately 20%-60% or more of the total area between the various structural members (e.g. strips 16 and stations 14) of the cap 12. In the present embodiment, the web open areas 100 occupy at least approximately 50% of the total space encompassed by the headset 12 (see also, FIGS. 12 and 17-18).

Referring back to FIGS. 4-5, the exemplary headset system 10 may have any suitable arrangement for receiving signals from the subject's brain. As indicated above, the present embodiment includes one or more wire leads 70 (e.g. EEG signal transmission wires) associated with the electrode stations 14 for receiving signals from the electrode 30 or related components (e.g. cover 50) therein and conveying the signals to a desired destination. The wire leads 70 may have any suitable form, configuration, construction and operation, and may receive the signals from the electrode 30 or related component(s) in any suitable manner and convey them to any desired destination. In this embodiment, at least one wire lead 70 is electrically coupled to an electrically-conductive surface 22 provided in each electrode aperture 20 and which conductively engages the associated electrode 30 (or associated component(s)). For example, the illustrated electrically-conductive surface 22 is slideably, electrically-conductively engaged by the exterior side surface 51 of the electrode cover 50 to receive the EEG signals therefrom.

Figure 16A:
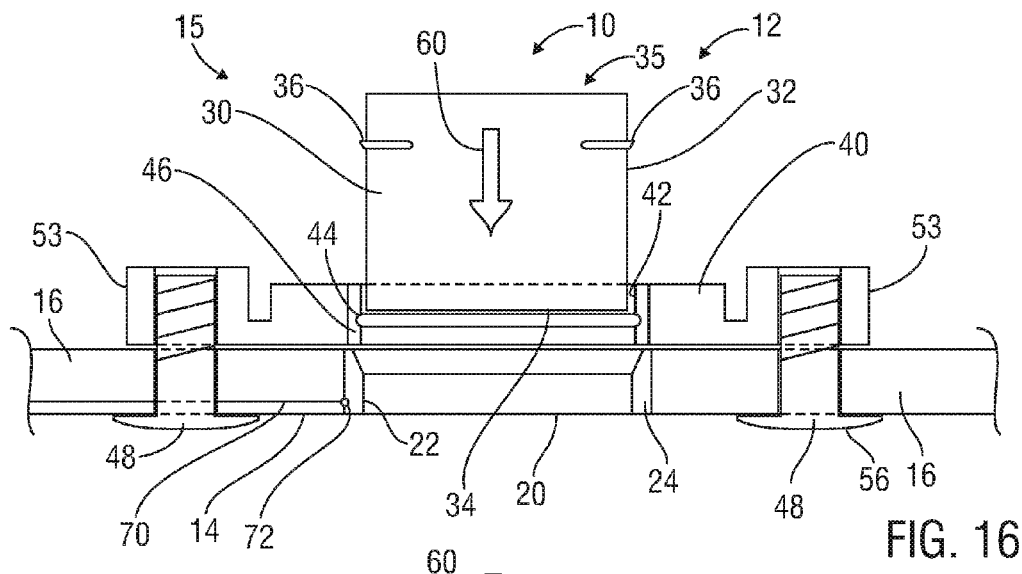
FIGS. 16A-B are side sectional views of part of the exemplary headset system of FIG. 12 showing an exemplary electrode being inserting into an exemplary electrode aperture in accordance with an embodiment of the present disclosure.

As shown in FIGS. 16A-17, the wire lead 70 may include a station end 72 electrically coupled to the electrically-conductive surface 22 and a device end 74 electrically coupled to any suitable desired measuring device(s) 108 (e.g. laptop computer). If desired, the headset 12 may include numerous wire leads 70, which may be bundled and/or interconnected. It should be noted that the measuring device 108, operation thereof and the electrical connection of the system 10 therewith is not limiting upon the present disclosure. For example, the system 10 may include an electrical connector 107 (e.g. FIG. 3) for electrically coupling the wire leads 70 to the measuring device(s) 108.

Referring back to the embodiment of FIGS. 4-5, the electrically-conductive surface 22 may have any suitable form, configuration and operation. In some embodiments, the electrically-conductive surface 22 may be provided on a metal tab or other configuration that at least partially lines an interior arc or portion of the aperture 20. In the illustrated embodiment, the electrically-conductive surface 22 is provided on an electrically-conductive ring 24 disposed in, or lining, the electrode aperture 20.

When included, the electrically-conductive ring 24 may have any suitable form, configuration and operation. For example, the illustrated ring 24 is rigid and includes first and second ring portions 24a, 24b which are snapped or friction-fit, and/or glued together. Further, the electrically-conductive ring 24 may have any desired construction as long as it allows the transmission of signals from an electrode 30 or related component(s) to at least one wire lead 70. In this embodiment, the ring 24 is constructed of tin, such as to provide sufficient electrical conductivity with low electrical noise, to minimally tarnish and/or other suitable purpose(s). In other embodiments, the electrically-conductive ring 24 may be made of any other suitable metal, such as gold, silver, copper, or aluminum, or a carbon composite. In some embodiments, the electrically-conductive ring 24 may include a metal plating or surfacing. In various embodiments, the electrically-conductive ring 24 may be constructed of a combination of the aforementioned or other materials.

Figure 9:
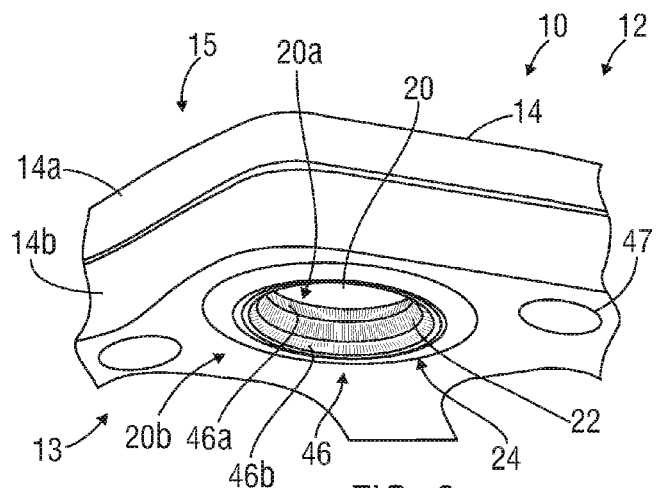
FIG. 9 is a perspective view of part of the exemplary headset system of FIG. 1 showing an exemplary electrode aperture.

It should be noted that the electrically-conductive ring 24 may serve one or more additional purposes. For example, the electrically-conductive ring 24 may also serve as an electrode retention ring (46) for assisting in positioning the associated electrode 30, such as will be described further below (e.g., FIGS. 4-5 and FIG. 9).

Still referring to the embodiment of FIGS. 4-5, the wire lead(s) 70 may conductively engage the electrically-conductive surface 22 in any suitable manner. In this particular configuration, the illustrated wire lead 70 is coupled to the electrically-conductive ring 24 via an electrically-conductive screw 71. However, the wire lead 70 could instead be soldered or coupled to the ring 24 in any other suitable manner, as desired.

Figure 13:
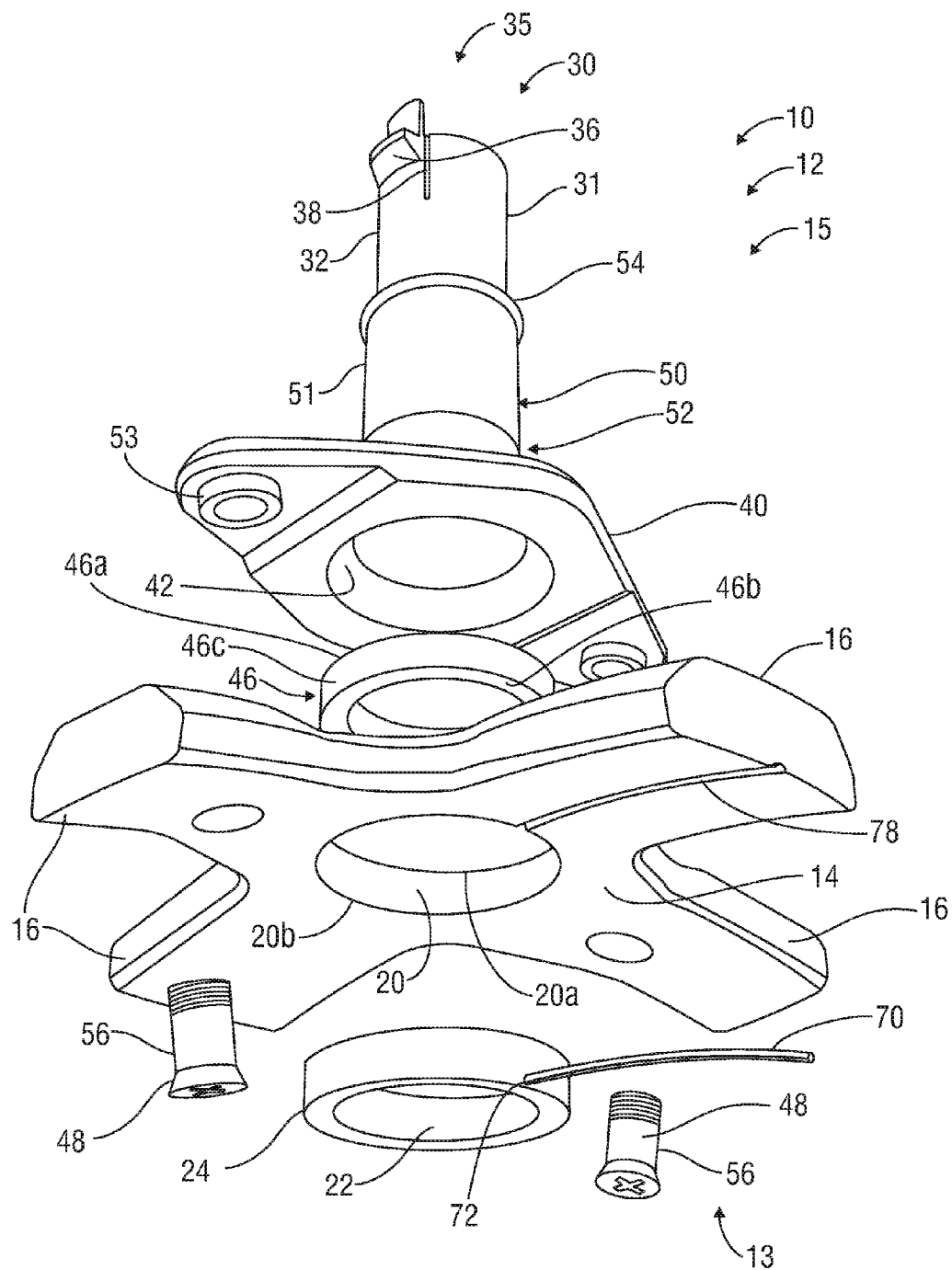
FIG. 13 is an exploded assembly view of part of the exemplary headset system of FIG. 12 showing an exemplary electrode station and related components.

The wire leads 70 may be positioned in or carried by the headset 12 in any suitable manner. In this embodiment, each wire lead 70 is at least partially or substantially hidden or sandwiched between the respective upper and lower layers 14a, 14b of the electrode stations 14 and the respective upper and lower layers 16a, 16b of the strips 16. In other embodiments, such as shown in FIG. 13, the wire leads 70 may lie in a series of recessed wire channels 78 formed in the inner side 13 of the cap 12. In yet other embodiments, the wire leads 70 may be carried internally within the stations 14 and strips 16 or otherwise coupled to the cap 12. In yet other embodiments, a wire harness including all the wire leads 70 may be enclosed within the cap 12 or affixed thereto.

In another independent aspect of the present disclosure, referring back to FIGS. 1-5, the electrodes 30 are biased into contact with the subject's head 98 sufficient to receive signals from the subject's brain in any suitable manner. In this embodiment, each electrode 30 is configured to be suspended within its associated electrode aperture 20 so that it effectively floats within a generally defined range of up-and-down motion relative to the aperture 20. At the same time, the exemplary biasing flap 40 provides downward biasing forces on the electrode 30.

During use, each illustrated biasing flap 40 independently places downward biasing forces on its associated electrode 30, while concurrently, the subject's head 98 typically places upward forces (e.g. arrow 64, FIGS. 5, 16C and 19C) on the electrode 30. As each individual exemplary electrode 30 freely floats (e.g. within a range-of-motion) relative to its associated aperture 20, the electrode 30 will automatically move into the appropriate up-and-down position between the biasing flap 40 and the subject's head 98 and relative to the headset 12 independent of all the other electrodes 30 in the headset 12. The position of each illustrated electrode 30 with thus be influenced or determined by the shape of the subject's head 98 at that location. Different electrodes 30 may assume different positions relative to the headset 12. Accordingly, since each exemplary electrode 30 fits the shape of the subject's head 98 at that location, the headset 12 may conform to the unique (typically uneven) shape of each subject's head 98. As compared to prior signal receiving headsets, the exemplary cap 12 may, for example, be more universally fittable and useful, more easily adaptable to the unique shape of different subjects' heads 98, provide better electrode positioning and electrical contact with the subjects' scalp test areas 104, be easier and quicker to successfully use, be more reliable or a combination thereof.

Referring again FIGS. 4-5, in many embodiments, the electrodes 30 may be moveable and positionable relative to the headset 12 between at least one retracted position (or range-of-motion) and at least one extended position (or range-of-motion) to assist in conforming the headset 12 to the shape of each subject's head 98, provide better electrode positioning and electrical contact with the subjects' scalp test areas 104, be easier and quicker to successfully use, be more reliable, any other desired purpose or a combination thereof. It should be noted that during use of this embodiment, in all retracted and extended positions the electrode 30 is biased in the direction of the subject's head 98 by its associated biasing flap 40.

In a retracted position, each exemplary electrode 30 is higher in its associated electrode aperture 20, and the bottom end 34 of the electrode 30 is closer to the inner side 13 of the headset 12, than in its extended position(s). In other words, in a retracted position, more of the illustrated electrode 30 lies above the electrode aperture 20 than in an extended position. The exemplary retracted position(s) may be useful, for example, as the initial position of the electrodes 30 during placement of the cap 12 on the subject's head. In many instances, the retracted position(s) of some, many or all the electrodes 30 may provide sufficient electrical conductivity with the subject's head 98, so that movement into an extended position may not be necessary.

Still referring to FIGS. 3 and 4, an extended position, more of the exemplary electrode 30 sits below the aperture 20 than above the aperture 20. The extended position(s) may be desirable or necessary, for example, for any electrodes 30 not making sufficient electrical contact with the scalp test area 104 after the cap 12 is fitted onto the subject's head 98.

The electrodes 30 may be moveable between retracted and extended positions in any desired manner. For example, to move an exemplary electrode 30 from a retracted position to an extended position, the flap 40 and electrode 30 may be pushed downwardly from above. To move the illustrated electrode 30 from an extended position to a retracted position, the bottom end 34 of the electrode 30 may be pushed upwardly. (See also, FIGS. 18-19C).

Figure 10A:
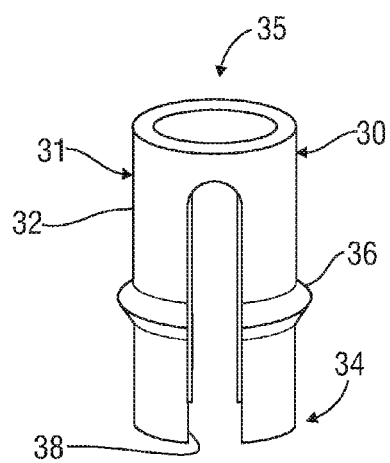
FIG. 10A is a perspective view of the exemplary electrode useful in the exemplary headset system shown in FIG. 1 in accordance with an embodiment of the present disclosure.
Figure 10B:
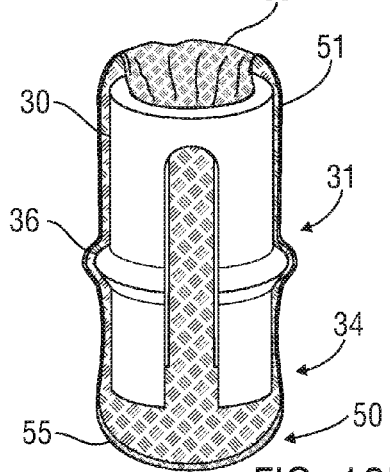
FIG. 10B is a perspective view of the exemplary electrode shown in FIG. 10A with an exemplary electrode cover shown in partial cross-section in accordance with an embodiment of the present disclosure.
Figure 10C:
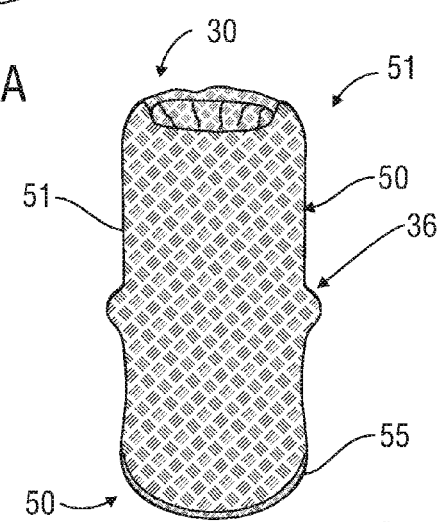
FIG. 10C is a perspective view of the exemplary electrode of FIG. 10B shown encapsulated by the exemplary illustrated electrode cover.

Now referring to FIGS. 10A-C, in some embodiments, the electrode 30 includes one or more protrusions 36 extending outwardly from at least one side 31 thereof. The protrusion(s) 36 (e.g. FIGS. 4-5) may be useful, for example, to assist in selectively positioning the electrode 30 relative to the headset 12 and/or subject's scalp 102 (e.g. height-wise and angle-wise (e.g. to conform substantially perpendicularly to the scalp 102)), provide more flexibility and greater degrees of freedom in the up-and-down movement of the electrode 30, assist in the movement of the electrode 30 between retracted and extended positions, secure the electrode 30 into one or more retracted or extended positions, provide a distinct range-of-motion of the electrode 30 in multiple respective retracted and extended positions, any other suitable purpose or a combination thereof.

The protrusions 36 may have any suitable form, configuration and construction. For example, one or multiple adjacent protrusion(s) 36 may extend partially or entirely around the outer side surface 32 of the electrode 30. In this embodiment, two aligned protrusions 36 form a circular ridge around the outer side surface 32 of the cylindrically-shaped electrode 30 at a desired height on the electrode 30. For example, the protrusion 36 may be spaced upwardly from the bottom end 34 of the electrode 30 by approximately ⅓ of the height of the electrode 30 to achieve the desired result(s) of use of the protrusion 36, such as described above. For some other examples, the protrusions 36 may be or include one or more rims, ledges, shelfs, cut-outs, uneven portions, buttons, hooks, pimples, channels or other-shaped members or portions extending at least partially around the side(s) 31 of the electrode 30. Further, when electrode covers 50 are included, the system 10 may be configured so that the covers 50 conform to the shape of the protrusion(s) 36 of the associated electrodes 30 (e.g. FIGS. 10B-C). In other embodiments, if desired, the protrusion 36 may penetrate through the electrode cover 50.

The protrusions 36 may have any suitable operation. Referring again to FIGS. 4-5, in this embodiment, when an electrode 30 is in a retracted position, the protrusion 36 will be closer to the outer side 15 of the headset 12 than the inner side 13. When the exemplary electrode 30 is in an extended position, the protrusion 36 will be closer to the inner side 13 of the headset 12 than the outer side 15.

If desired, the protrusion 36 may be useful to establish and/or secure the desired position of the electrode, such as in the extended and/or retracted positions. For example, the protrusion 36 may be engageable with the electrode aperture 20, or other component(s), in one or more positions. In some embodiments, the protrusion 36 may be configured to releasably selectively engage the upper edge 20a of the aperture 20 and/or the lower edge 20b of the aperture 20 (see also, FIGS. 13, 19B), one or more grooves 44 (e.g. FIGS. 16B-C) or other protrusion-engagement surface(s) provided in the aperture 20 or other component (e.g. upper and lower edges 46a, 46b of an electrode retention ring 46 (see also, FIG. 19B)), or a combination thereof.

Figure 16B:
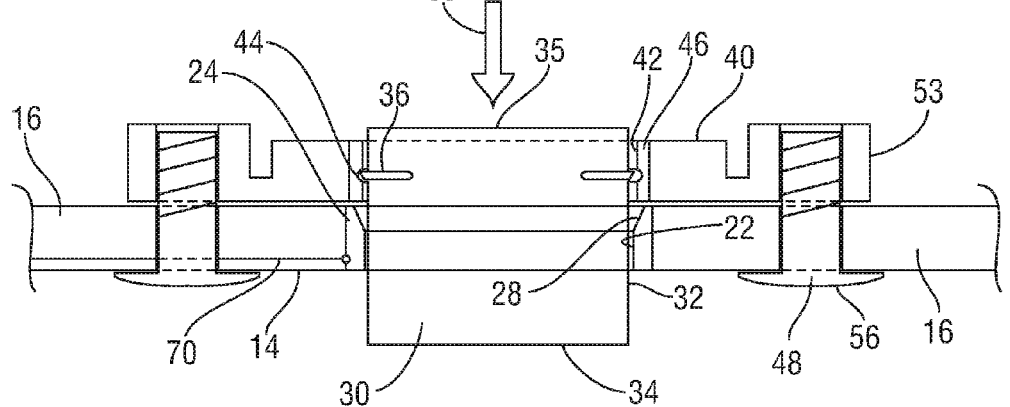
Figure 16C:
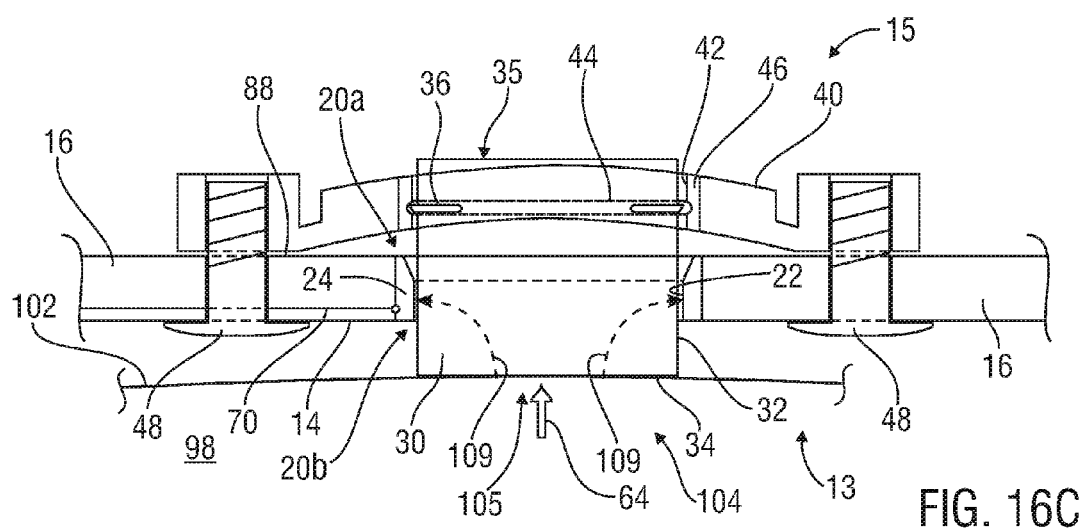
FIG. 16C is a side sectional view of the part of the exemplary headset system of FIG. 12 shown in FIGS. 16A-B showing the illustrated exemplary electrode being biased between an exemplary electrode biasing flap and a subject's head in accordance with an embodiment of the present disclosure.

In the embodiment of FIGS. 16A-C, the protrusion 36 is selectively, releasably engageable with a groove, or catch, 44 provided in the flap hole 42 of the biasing flap 40. In this example, the electrode 30 is insertable downwardly (arrow 60, FIGS. 16A-B) into the illustrated flap hole 42 to snap the protrusion 36 into releasable engagement with the illustrated groove 44. In this position, the exemplary electrode 30 is effectively anchored to the flap 40. As the illustrated flap 40 flexes, the electrode 30 moves, or floats up and down in and relative to the electrode aperture 20 in response to upward forces from the subject's scalp 102 during use (e.g. arrow 64, FIG. 16C).

In this embodiment, the electrode 30 is thus movable into only one engaged position, and the exemplary flap 40 serves the dual-purpose of biasing and retaining the electrode 30. However, in other embodiments, additional engaged positions may be provided, such as with multiple grooves 44 or other engagement surfaces in the flap hole 42 or other component. The use of one or more grooves 44 or other protrusion engagement surface(s) may be useful to selectively positioning the electrode 30 relative to the headset 12 and/or subject's scalp 102 (e.g. height-wise and angle-wise (e.g. to conform substantially perpendicularly to the scalp 102)), provide a distinct range-of-motion of the electrode 30 relative to the headset 12, any other suitable purpose or a combination thereof.

Figure 26A:
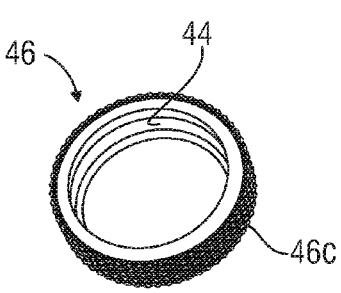
FIG. 26A is a perspective view of an exemplary electrode retention ring useful in various embodiments of headset systems in accordance with one or more embodiments of the present disclosure.
Figure 26B:
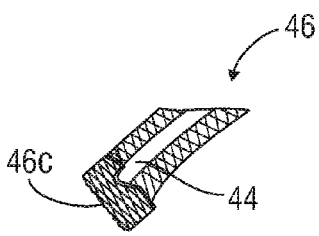
FIG. 26B is a perspective view of part of the exemplary electrode retention ring shown in FIG. 26A.

Still referring to FIGS. 16A-C, if desired, the groove 44 or other protrusion engagement surface of the flap hole 42 may be formed in an electrode retention ring 46 disposed within, or lining, the flap hole 42. The retention ring 46 may have any suitable form, configuration and operation. In this embodiment, for example, the retention ring 46 is rigid, constructed of plastic, molded into the flap 40 and includes a textured outer surface 46c (e.g. FIGS. 26A-B) for gripping the flap hole 42 to secure them together.

In some embodiments, the groove, or catch, 44 may be configured (e.g. with one or more angled edges or polarized) to assist in selectively positioning the electrode 30 relative to the headset 12 and/or subject's scalp 102 (e.g. height-wise and angle-wise (e.g. to conform substantially perpendicularly to the scalp 102)), promote movement of the electrode 30 in a desired direction for removal (such as downwardly) or other purpose. In this example, once the electrode 30 is inserted and snapped into the groove 44 from above (from the outer side 15 of the headset 12), the electrode 30 may be easily, or only, removed by pushing downwardly on the electrode 30 to release it from the groove 44, flap hole 42 and electrode aperture 20. In other embodiments, the groove, or catch, 44 may be configured to promote or require (i) upward insertion and removal of the electrode 30 from underneath (from the inner side 13 of the headset 12), (ii) upward insertion and downward removal, (iii) downward insertion and upward removal, or (iv) unidirectional insertion and removal.

Referring back to the embodiment of FIGS. 4-5, in this example, the illustrated electrically-conductive ring 24 also serves as the electrode retention ring 46 and does not include a groove 44. In this example, the relationship of the illustrated electrode protrusion 36 relative to the electrode retention ring 46 determines whether the electrode is in a retracted or extended position. For example, the protrusion 36 may be shaped and sized so that it sits above the electrode retention ring 46 (closer to the upper edge 46a of the ring 46 than the lower edge 46b) when the electrode 30 is in a retracted position, and below the electrode retention ring 46 (closer to the lower edge 46b of the ring 46 than the upper edge 46a) when the electrode 30 is in an extended position. From either position, with sufficient pressure on the exemplary electrode 30, the protrusion 36 is moveable between a retracted position and an extended position. Thus, the illustrated protrusion 36 is forcibly, selectively, slideable up and down through the retention ring 46. For example, the protrusion 36 may be designed to be movable through the ring 46 under only certain applied pressure. For example, when the protrusion is below the retention ring 46 (the electrode 30 in an extended position), the system 10 may be designed so that the typical or expected upward forces from the subject's head 98 during fitting and use of the headset 12 will not dislodge the protrusion 36 upwardly through the ring 46.

Still referring to FIGS. 4-5, in some embodiments, the protrusion 36 and/or the upper and/or lower edges 46a, 46b of the electrode retention ring 46 may be shaped to complement each other, such as to assist in selectively positioning the electrode 30 relative to the headset 12 and/or subject's scalp 102 (e.g. height-wise and angle-wise (e.g. to conform substantially perpendicularly to the scalp 102)), assist in the desired direction of insertion/removal of the electrode 30 into/from the headset 12, other suitable purpose or a combination thereof. For example, the outer curvature of the protrusion 36 (e.g. FIG. 10A), may match the curvature of the edges 46a, 46b (e.g. FIG. 9) of the ring 46 so that the protrusion will seat in the upper and lower edges 46a, 46b in respective retracted and extended positions. In the illustrated embodiment, the upper and/or lower edges 46a, 46b of the electrode retention ring 46 are beveled (e.g. FIG. 9) to compliment the shape of the protrusion(s) 36.

Also if desired, the movement of the protrusion 36 above or below the electrode retention ring 46 may provide additional positions for the electrode 30. In the present embodiment, the electrode 30 can freely move within a defined up and down range-of-motion above the electrode retention ring 46 among multiple retracted positions and below the electrode retention ring 46 among multiple extended positions.

Figure 19A:
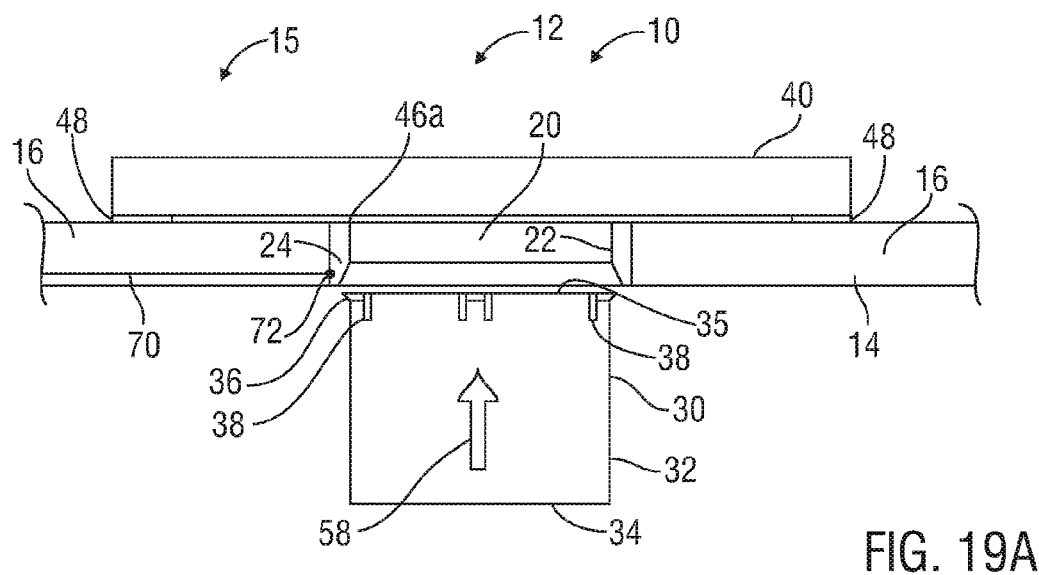
FIGS. 19A-B are side sectional views of part of the exemplary headset system of FIG. 18 showing an exemplary electrode being inserting into an exemplary electrode aperture in accordance with an embodiment of the present disclosure.
Figure 19B:
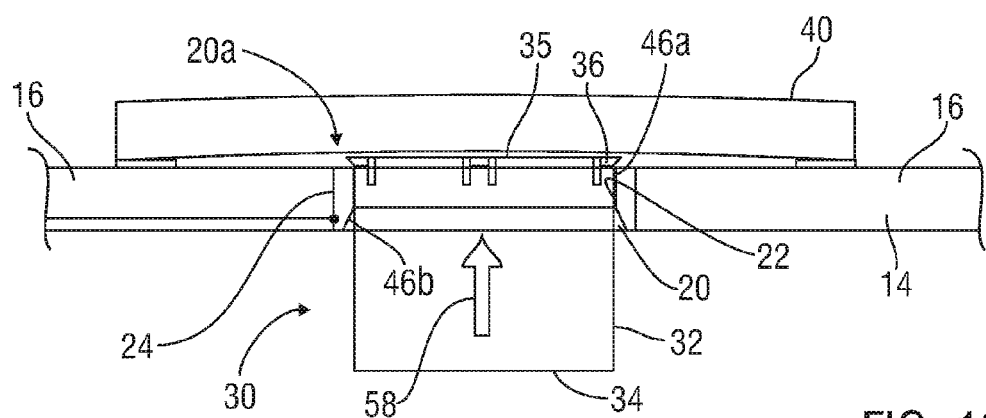
Figure 19C:
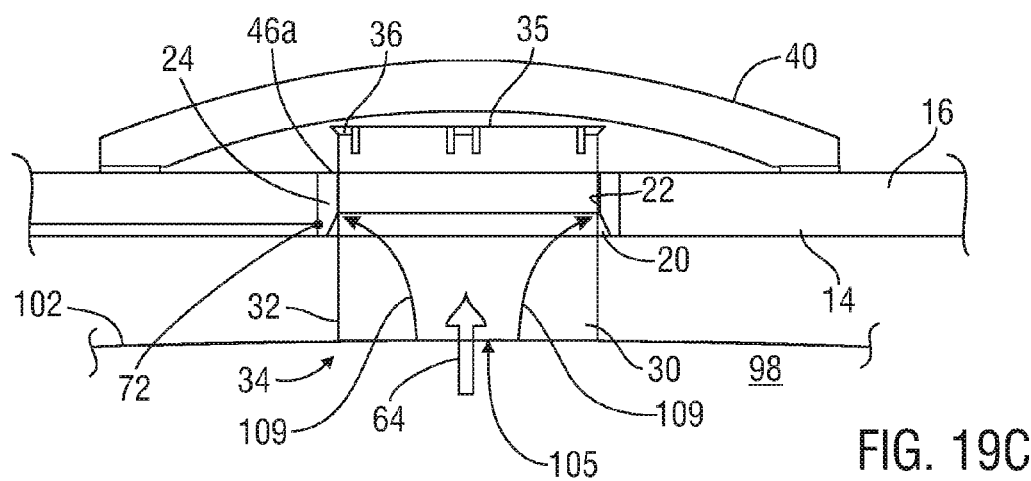
FIG. 19C is a side sectional view of the part of the exemplary headset system of FIG. 18 shown in FIGS. 19A-B showing the illustrated exemplary electrode being biased between an exemplary electrode biasing flap and a subject's head in accordance with an embodiment of the present disclosure.

In the embodiment FIGS. 19A-C, the protrusion 36 is located proximate to the top end 35 of the electrode 30 and releasably engageable with the upper edge 46a of the retention ring 46 into and out of one extended position. In this embodiment, the electrode 30 is moveable within a defied range-of-motion in multiple extended positions (above the electrode aperture 20) due to the upward forces (arrow 64, FIG. 19C) placed upon it by the subject's head 98.

Figure 21A:
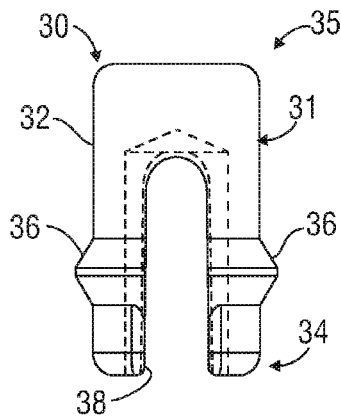
FIG. 21A is a side view of the exemplary electrode shown in FIG. 10A.
Figure 21B:
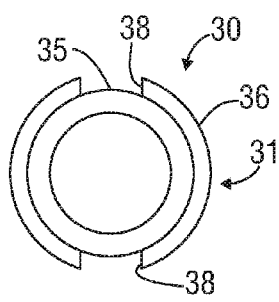
FIG. 21B is a top view of the exemplary electrode of FIG. 21A.
Figure 23:
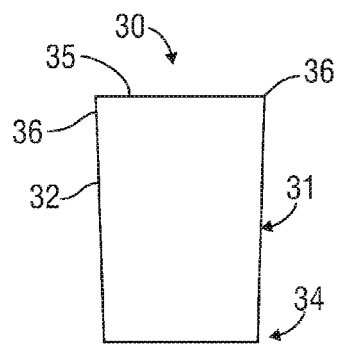
FIG. 23 is a side view of an exemplary electrode in accordance with another embodiment of the present disclosure.

Referring now to FIGS. 21A-B, the electrodes 30 may have any suitable form, configuration, components and operation. The electrode 30 may be a single unitary component or multiple interconnected units. For example, in the exemplary embodiment, the electrode 30 is a single unit having a generally cylindrical outer shape. Some other exemplary outer shapes of electrodes 30 are square, triangular, oval, stepped and rectangular. In FIG. 23, the exemplary electrode 30 has an upwardly-angled, or flared, outer shape, such as for ease or insertion from above into the flap hole 42 and/or electrode aperture 20. In other embodiments, the electrode 30 may have a downwardly-angled, or flared outer shape, such as for ease or insertion from below into the electrode aperture 20 and/or flap hole 42.

In some embodiments, the electrode 30 is at partially formed of memory foam (e.g. FIG. 23). Memory foam electrodes 30 may have any desired form, configuration and operation. For example, memory foam electrodes 30 may be useful at certain location on the head 98, such as portions with no hear (e.g. the forehead or on the entire head 98 of a bald subject).

In some embodiments, some or all of the electrodes 30 may be configured to be useful without electrode covers 50. For example, the bottom end 34 of the electrode 30 may be electrically conductive to the outer side surface 32 thereof. In such embodiments, the bottom end 34 may electrically conductively contact the scalp 102 and receive signals from the subject's brain. Those signals may then be electrically communicated to the outer side surface 32 of the electrode 30, then to the electrically-conductive surface 22 in the electrode aperture 20, and then to the lead wire 70.

Still referring to FIGS. 21A-B, the electrode 30 may be constructed of any suitable material, such as plastic, rubber, paper, fiberglass, wood, material tolerant of one or more conductive solutions, carbon-containing material, or a combination thereof. In some embodiment, the electrodes 30 are constructed of fluid absorbing material, such as foam and/or electrically-conductive material, such as conductive polymer material.

Figure 22:
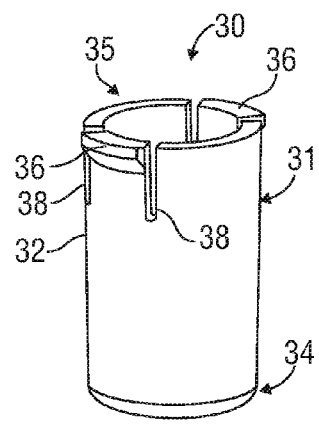
FIG. 22 is a perspective view of an exemplary electrode in accordance with another embodiment of the present disclosure.

In various embodiments, the top and/or bottom ends 35, 34 of the electrode 30 may be open, include one or more perforation or be closed. In the present embodiment, both the top end 35 and bottom end 34 are open. In the embodiment of FIGS. 13 and 22, the top end 35 of the electrode 30 is open, while the bottom end 34 is at least substantially closed (e.g. may include one or more perforation for engagement with an internally-located flexible electrode stabilizing insert). In some embodiments, the bottom end 34 of the electrode 30 may be textured or rough, such as to improve contact and electrical conductivity with the scalp 102, be rubbed against the scalp 102 to exfoliate the skin to assist in attaining good electrical conductivity, other suitable purpose or a combination thereof.

Figure 14:
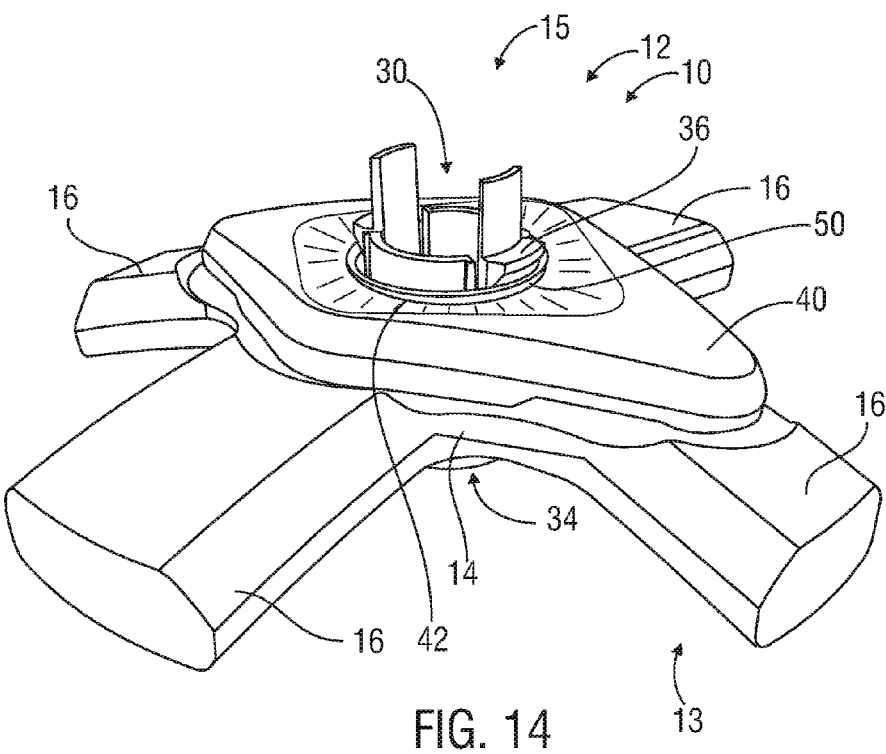
FIG. 14 is a perspective view of the exemplary electrode station and related components of FIG. 13.
Figure 15:
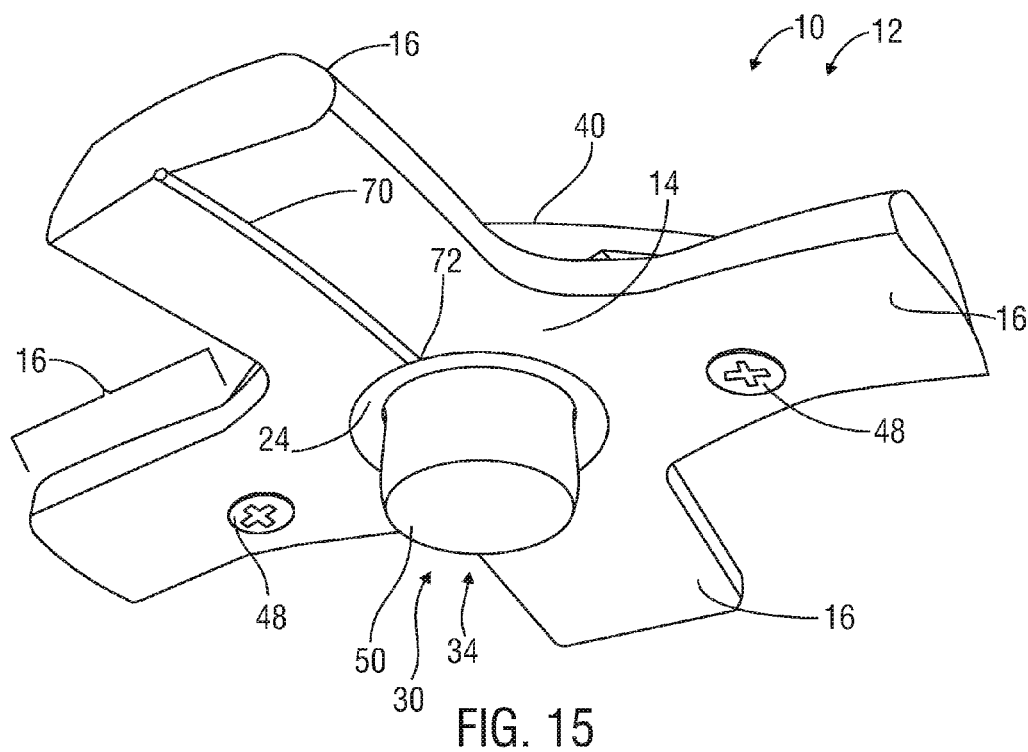
FIG. 15 is another perspective view of the exemplary electrode station and related components of FIG. 13.

Still referring to FIGS. 21A-B, in some embodiments, the electrode 30 includes one or more cut-outs, or flex slots, 38. The cut-out(s) 38 may be included for any purpose, such as to allow the electrode 30 to flex during insertion and/or removal from the electrode aperture 20 and/or flap 40. For example, the cut-out(s) 38 may allow the electrode 30 to be easily squeezed and snapped into place, and once in place in the headset 12, squeezed to be removed therefrom. The flex slots 38 may have any suitable form, configuration and operation. In the present embodiment, two cut-outs 38 extend from the bottom end 34 of the electrode 30 up to a desired location along the height of the side 31 (see also, FIGS. 4-5, 10A-B). The illustrated flex slots 38 may be useful, for example, for squeezing the electrode 30 proximate to its bottom end 34, or allowing the electrode 30 to flex thereabouts, during upward insertion and downward removal of the electrode 30 into/from the electrode aperture 20. In the embodiment of FIGS. 14 and 22, four cut-outs 38 are shown extending from the top end 35 of the electrode 30 to a desired location along the height of the side 31. The flex slots 38 in this embodiment may be useful, for example, for squeezing the electrode 30 proximate to its top 35, or allowing the electrode 30 to flex thereabouts, during downward insertion and downward removal of the electrode 30 into/from the electrode apertures 20.

Now referring to FIGS. 10B-C, the electrode cover 50 may have any suitable form, configuration, construction and operation. The cover 50 may or may not completely encapsulate the electrode 30 and may or may not be glued or otherwise secured to the electrode 30, as desired. When it is desired to secure the cover 50 to the electrode 30, any suitable technique may be used. For example, the cover 50 may include a draw string, elastic band(s) or the like that may be tightened to assist in retaining the cover 50 on the electrode 30. For another example, the cover 50 may be glued and/or heat-welded to the electrode 30. In some embodiment, the cover 50 may tightly fit and grip the electrode 30 without glue or any coupling mechanism.

Figure 24A:
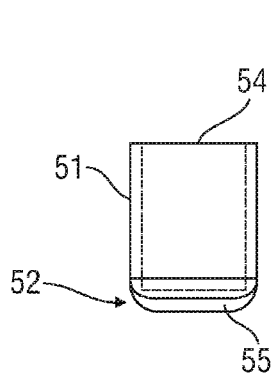
FIG. 24A is a side view of an exemplary electrode cover in accordance with an embodiment of the present disclosure.
Figure 24B:
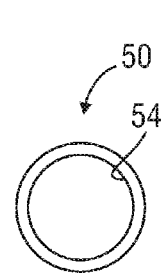
FIG. 24B is a top view of the exemplary electrode cover of FIG. 24A.

In the present embodiment, the exemplary cover 50 completely encapsulates the electrode. The illustrated cover 50 has an upper sock opening 54 for slipping the cover 50 over the bottom end 34 of electrode 30 that is tucked into the open top end 35 of the electrode 30. The illustrated cover 50 is glued or heat-welded around the opening 54 to close off the opening 54 and may also be glued or heat-welded thereabout to the inside of the electrode 30. In the embodiment of FIGS. 24A-B, the cover 50 will not completely encapsulate, and is not secured to, the electrode 30.

When the cover 50 is constructed of electrically-conductive liquid 90 absorbing material, the cover 50 may be constructed at least partially of cotton, natural or synthetic conductive material, fibers or fabric, any other liquid-absorbing and electrically-conductive material or a combination thereof. In some embodiments, multiple conductive fibers (not shown) may be woven into the cover 50 for lowering contact and/or path resistance. In various embodiments, the cover 50 may be at least partially constructed of exfoliating material (e.g. nylon), as is known and used in beauty industry, and/or have a textured or rough surface at the bottom end 52 thereof.

Figure 25:
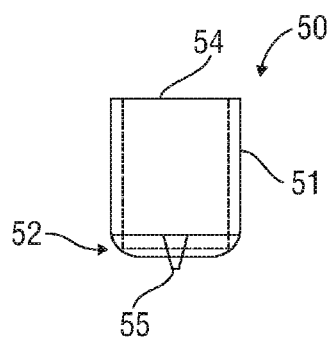
FIG. 25 is a side view of an exemplary electrode cover in accordance with another embodiment of the present disclosure.

Still referring to FIGS. 10B-C, if desired, the cover 50 may have a seam 55 disposed at the bottom end 52 of the cover 50 (see also, FIG. 25). The seam 55 may have any suitable form, configuration and operation. For example, the seam 55 may accumulate more electrically-conductive liquid 90 than the remainder of the cover 50, extend further into the subject's hair and against the scalp 102 than the body of the cover 50, be coarse or thick and useful to exfoliate the subject's scalp 102 if the electrode 30 is rotated or otherwise moved while in contact with the scalp 102, any other suitable purpose or a combination thereof.

Referring again to FIGS. 4-5, 12 and 18, in other independent aspects of the present disclosure, in some embodiments, the electrode 30 may be movable within the electrode aperture 20 as it engages the subject's scalp 102. For example, the electrode 30 may be rotatable to maneuver through the subject's hair and/or scrub, abrade or exfoliate one or more epidermal layers of the scalp 102 for improving electrical conductivity. As the exemplary electrode 30 is rubbed against the subject's scalp 102, the electrode 30 (or cover 50 thereon) may be used to rub, scrub, clean or abrade the scalp 102 to exfoliate the scalp 102 or remove dead skin therefrom, such as to assist in achieving better electrical contact and conductivity. The use of an electrode 30 (with our without cover 50) to rub, exfoliate or prepare the scalp for use of the headset system 10, such as described above, could be used instead of a blunt needle typically rubbed against the scalp to remove dead skin, exfoliate or otherwise prepare the scalp for use during such testing.

The electrodes 30 may be formed in different sizes, shapes and configurations. In some embodiment, the electrodes 30 may be replaceable on a per patient basis, such as for cleanliness, optimizing electrical conductivity (if they dry out or are calibrated for wetness) or other purpose. In various embodiments, different electrodes 30 may be used on the headset 12 for a particular subject and/or at different locations in the cap 12, such as to improve electrical conductivity or for other reasons. For example, different sized, shaped or configured electrodes 30 may be provided to accommodate different electrode positions on the cap 12 for a particular subject to improve or optimize electrical conductivity at each location. For another example, electrodes 30 constructed of different materials and/or some with and some without covers 50 may be used for a particular subject.

For use of the exemplary systems 10, the electrodes 30 (or covers 50, when included) are laden with one or more electrode wetting agents to provide or enhance electrical conductivity.

Referring back to FIGS. 1-5, in another independent aspect of the present disclosure, an electrically-conductive liquid, or formula, 90 may be placed upon each electrode 30 (and/or cover 50, when included) as the electrode wetting agent. For example, the electrically-conductive liquid 90 may be useful to lower contact resistance at the scalp and/or to lower path resistance for signal flow (e.g. arrows 109, FIG. 19C) from the bottom end 34 of the electrode 30 to wire lead 70 to a desired level. In many embodiments, the electrically-conductive liquid 90 may be designed to possess electric conductivity attributes that will allow or match the input impedance specified for the particular signal amplifier of the test (EEG or other brainwave measurement) system being used. In some embodiments, for example, the electrically-conductive liquid 90 may be designed to possess electrical conductivity attributes that allow the electric path resistance for signal flow (e.g. arrows 109, FIG. 16C) to be maintained at less than 80 k ohms, and, in some instances, less than 40 k ohms and, in some instances, less than 5 k ohms impedance.

The electrically conductive liquid 90 may have any suitable composition and properties. In accordance with various embodiments, the electrically-conductive liquid 90 includes a hair conditioner and/or an optical/contact lens solution. In some embodiments, such as when a gel would normally be used during the test, the electrically-conductive liquid 90 may include the hair conditioner, such as, for example a "leave-in" hair conditioner. This form of electrically-conductive liquid 90 may be combed into the hair after the test and the hair may be returned to its normal appearance. The use of hair conditioner in the electrically-conductive liquid 90 may also, in at least some situations, serve the function of nourishing the hair. The use of hair conditioner in the electrically-conductive liquid 90 may also allow typical subjects to resume their day or nighttime activities without having to wash their hair. For example, if the test is conducted during a routine physical exam, the subject may be able to immediately return to work or his/her other activities, as opposed to having to first wash his/her hair.

When used in the electrically-conductive liquid 90, the hair conditioner may have any suitable ingredients and liquid properties. One example presently commercially available leave-in conditioner that could be included in, or used as, the electrically-conductive liquid 90 in some embodiments is "PAUL MITCHELL® THE CREAM® Leave-in Conditioner and Styler", having the following ingredients: Water, PVP, Glycerin, Yeast (Faex) Extract, Methyl Gluceth 10, Stearalkonium Chloride, *Simmondsia Chinensis* (Jojoba) Seed Oil, *Carthamus Tinctorius* (Safflower) Seed Oil, Amodimethicone, Bisamino PEG/PPG 41/3 Aminoethyl PG Propyl Dimethicone, Panthenol, Ethylhexyl Methoxycinnamate, Benzophenone 4, Guar Hydroxypropyltrimonium Chloride, Cetearyl Alcohol, Hydroxyethylcellulose, Polysorbate 60, Phenoxyethanol, C11 15 Pareth 7, Trideceth 12, Laureth 9, Citric Acid, Methylparaben, Propylparaben, Disodium EDTA, Diazolidinyl Urea, Fragrance, Hexyl. In various embodiments, an exemplary electrically-conductive liquid 90 may include any particular two or more of the above-listed ingredients.

Another example presently available leave-in conditioner that could be included in, or used as, the electrically-conductive liquid 90 in various embodiments is "Generic Value Products Cream", presently available at Sally Beauty Supply, LLC as Sally Item No. SBS-264043 and having the following ingredients: Water (Aqua), PVP, Glycerin, Yeast Extract, Methyl Gluceth-10, Stearalkonium Chloride, *Simmondsia Chinensis* (Jojoba) Seed Oil, *Carthamus Tinctorius* (Safflower) Oil, Amodimethicone, Bisamino PEG/PPG-41/3 Aminoethyl PG-Propyl Dimethicone/Hedychium Coronarium (White Ginger)/PEG-12 Dimethicone, Panthenol, Ethylhexyl Methoxycinnamate, Benzophenone-4, Guar Hydroxypropyltrimonium Chloride, Cetyl Alcohol, Cetearyl Alcohol, Hydroxyethylcellulose, Polysorbate-60, Phenoxyethanol, C11-15 Pareth-7, Trideceth-12, Laureth-9, Citric Acid, Fragrance (Parfum), Methylparaben. In many embodiments, an exemplary electrically-conductive liquid 90 may include any particular two or more of the above-listed ingredients. However, the present disclosure is not limited to these particular examples.

In some embodiments, the electrically-conductive liquid 90 includes optical/contact lens solution. In various embodiments, the optical/contact lens solution may provide eye soothing and/or disinfecting benefits and/or be less sticky.

When included in the electrically-conductive liquid 90, the optical/contact lens solution may have any suitable ingredients and liquid properties. For example, one presently commercially available optical/contact lens solution that could be included in some embodiments of the electrically-conductive liquid 90 is "Renu Sensitive Multi-Purpose Solution" by Bausch & Lomb Incorporated and having the ingredients of a sterile, isotonic solution that contains boric acid, edetate disodium, poloxamine, sodium borate and sodium chloride; preserved with DYMED® (polyaminopropyl biguanide) 0.00005%. In many embodiments, an exemplary electrically-conductive liquid 90 may include any particular two or more of the above-listed ingredients. However, the present disclosure is not limited to this particular example.

Figure 11A:
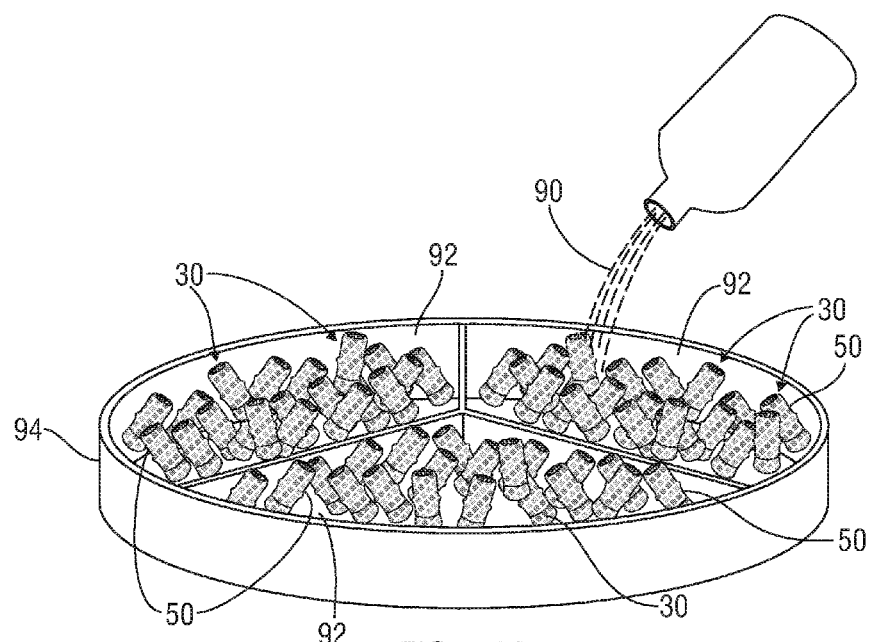
FIG. 11A is a perspective view of an exemplary tray of an exemplary electrode storage system in accordance with an embodiment of the present disclosure.
Figure 11B:
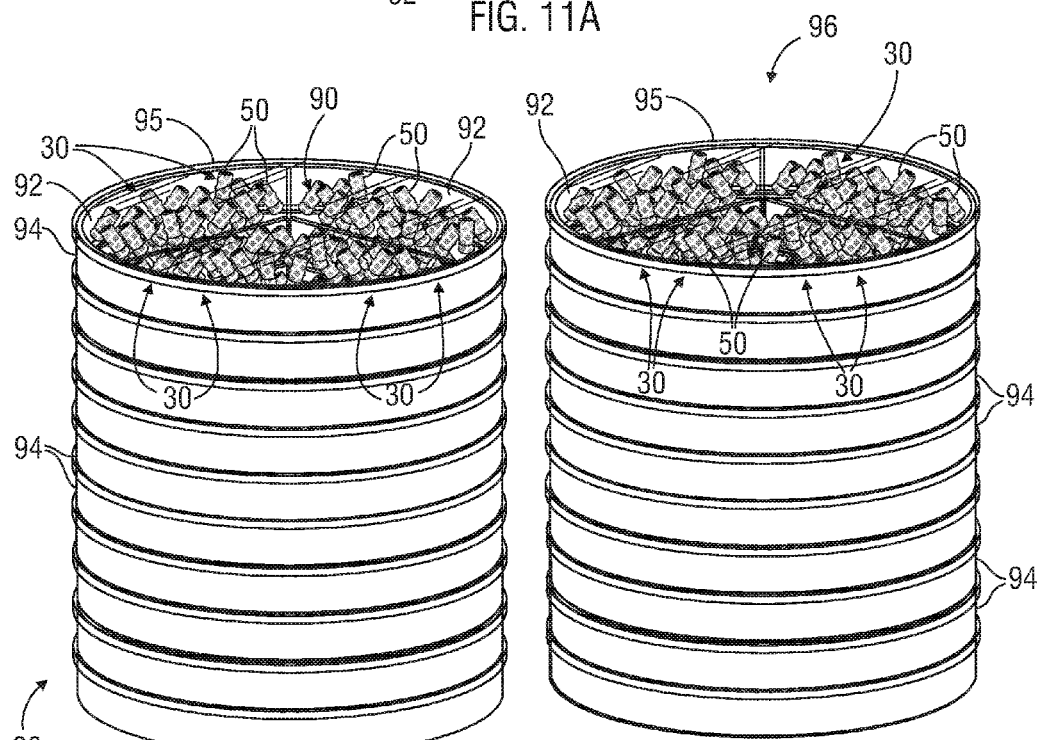
FIG. 11B is a perspective view of an exemplary electrode storage system in accordance with an embodiment of the present disclosure.
Figure 12:
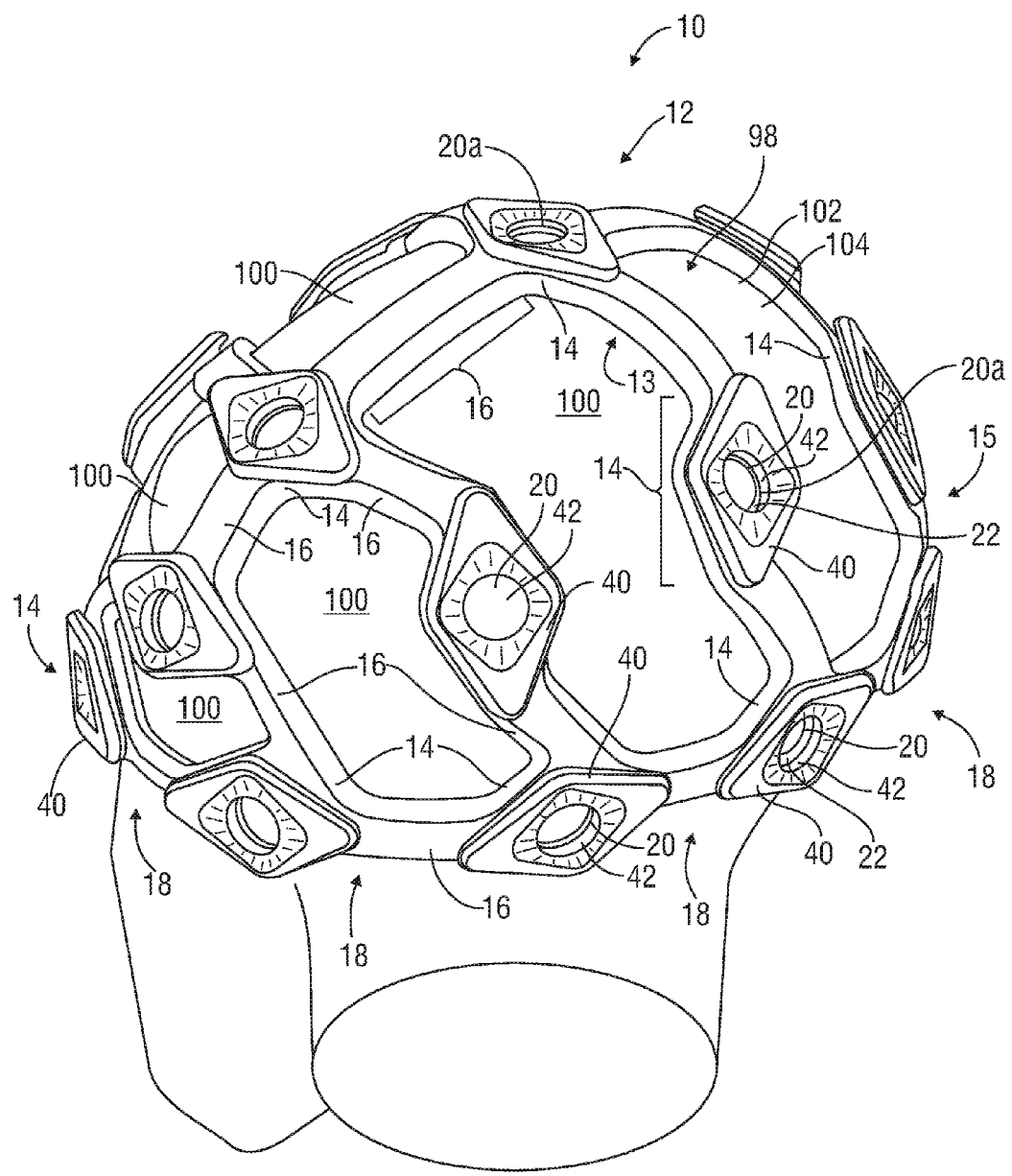
FIG. 12 is a perspective view of an exemplary signal receiving headset system shown positioned on a human subject's head in accordance with another embodiment of the present disclosure.

The electrodes 30 (or covers 50) may be laden with the electrically-conductive liquid 90 in any suitable manner. In some embodiments, the electrodes 30 may be first inserted into the headset 12 and then laden with electrically-conductive liquid, such as with a squirt bottle or other applicator. In other embodiments, for example, the electrodes 30 (with our without the covers 50) may be pre-packaged wet with the electrically-conductive liquid 90. For example, the pre-soaked electrodes 30 may be stored in a sealed plastic pouch. For another example, in the embodiment of FIGS. 11A-B, the necessary quantity of electrodes 30 for the desired test is prepackaged in separate sections 92 of distinct plastic electrode trays 94 of an electrode storage system 96. In this example, three distinct tray sections 92 each hold twenty electrodes 30 (for a typical EEG test), and ten trays 94 are shown stacked and releasably engaged upon one another for ease of storage, delivery, transport, etc. When the associated headset 12 needs to be fitted with a set of electrodes 30, a tray 94 is uncovered (e.g. by removal of a cover 95 or an upper tray 94) and the electrically-conductive liquid 90 is squirted, sprayed or poured onto the electrodes 30 in a first tray section 92, preserving the dry status of the other electrodes 30 in the tray 94 and storage system 96 for future use.

Referring to FIGS. 1-5, the electrically-conductive liquid laden electrodes 30 may then be inserted in to the headset 12 (see also, FIGS. 12-19C). The exemplary headset system 10 may then be placed and/or fitted on the subject's head 98 so that each (electrically-conductive liquid laden) electrode 30 is positioned to contact the scalp 102 as desired. However, if the contact between any electrode 30 is not satisfactory or for any other suitable reason, the administrator of the test may add additional electrically-conductive liquid 90 between the electrode 30 and the scalp 102. For example, additional electrically-conductive liquid 90 containing optical/contact lens solution may be inserted between the electrode 30 and scalp 102, such as with a squirt bottle, blunt needle, plastic syringe or other applicator. For another example, electrically-conductive liquid 90 containing hair conditioner may be inserted between the electrode 30 and scalp 102, such as with a squirt bottle, tube, blunt needle, plastic syringe or other applicator.

In some scenarios, electrically-conductive liquid 90 in the form of both the optical/contact lens solution and hair conditioner may be added between an electrode 30 and the scalp 102. For example, if the optical/contact lens solution is added and does not sufficiently enhance the desired electrical conductivity, the hair conditioner may then be added. For another example, if it is desirable to avoid dripping of the electrically-conductive liquid 90 at or around a particular electrode site, the hair conditioner (or an electrically-conductive liquid 90 with a mixture of ingredients that includes hair conditioner) may be preferred. It may be desirable to avoid dripping of the electrically-conductive liquid 90, for example, at electrode sites at locations that may be more prone to dripping, such as along the side of the subject's head 98. For example, if added electrically-conductive liquid 90 would be likely drip onto an area of the scalp 102 between adjacent electrodes 30, the dripped electrically-conductive liquid 90 could cause the signal measurements of adjacent electrodes 30 to be distorted. At such electrode sites, it may thus be desirable to use the hair conditioner as the (added) electrically-conductive liquid 90 because it is less likely to drip.

In some scenarios, the subject may have a preference as to which electrically-conductive liquid 90 to use on their head 98. For example, subject's having hair that has been straightened may have a heightened desire not to wet their hair because wetting may reverse or remove the straightening. In such instances, the subject may prefer the use of the hair conditioner-type electrically-conductive liquid 90 to preserve the straightening of their hair. Another exemplary situation where it may be preferred to add the hair conditioner instead of optical/contact lens solution is when the viscosity or thickness of the electrically-conductive liquid 90 is important. This may be the case, for example, when the headset 12 is placed or fitted onto the subject's head 98 and a gap exists between one or more of the electrodes 30 and the scalp 102. For example, the subject's hair style (e.g. cornrows) may not allow an electrode 30 to get close enough to the scalp 102 to sufficiently receive signals from the subject's brain. In such instance, the thickness or viscosity of the hair conditioner may fill the gap between the electrode 30 and scalp 102 sufficient to provide acceptable conductivity between the head and the electrode 30.

In some embodiments, the electrodes 30 (laden with electrically-conductive liquid) may be first positioned in the headset 12 in a retracted position. Thereafter, the headset 12 may be fitted onto the subject's head 98 without dripping the electrically-conductive liquid all over the head 98 or dragging the moist electrodes 30 across or along the subject's head 98. After the headset 12 is positioned on the subject's head 98, each electrode 30 may then, if necessary, be moved into an extended positioned into contact with or proximate to the subject's scalp 102 without dripping or dragging. In some instances, good contact is made with the scalp 102 and the signal transmission path from the scalp 102 to the electrode 30 is acceptable. However, after the test is initiated, if the electrical impedance or conductivity is insufficient, additional electrically-conductive liquid 90 (e.g. optical/contact lens solution, hair conditioner or a combination thereof) may be added as needed.

In various embodiments, the present disclosure may include any of the features mentioned above and/or one or more of the following features: a lightweight headset system 10 that adjustably conforms to a wide range of head sizes and shapes; a headset system 10 having electrodes 30 that may be visibly inspected and adjusted for one or more purposes, such as to make adjustments or changes to improve electrical conductivity and signal transmittal (e.g. accommodate a wide range of hair types, skin dryness, patient sensitivities to pressure, etc.); a headset system 10 that may be inexpensively reused and shared with multiple patients with less risk of transfer dirt, oil, germs. etc.; electrodes 30 that are replaceable and/or may be replaced with another style, size or configuration electrode 30; an electrically-conductive liquid 90 useful between the electrodes 30 and the subject's head 98 may be used to provide sufficient electrical conductivity for subjects with different hair styles and conditions, does not require washing or cleaning the hair and scalp after the test or any combination thereof; or a combination thereof.

Preferred embodiments of the present disclosure thus offer advantages over the prior art and are well adapted to carry out one or more of the objects of this disclosure. However, the claimed invention of any particular claim(s) does not require each of the components and acts described above and is in no way limited to the above-described embodiments or methods of operation, except and only to the extent as may be explicitly recited in one or more of the appended claims and only for those claims and any claims depending therefrom. Any one or more of the above components, features and processes may be employed in any suitable configuration without inclusion of other such components, features and processes. Moreover, the present invention includes additional features, capabilities, functions, methods, uses and applications that have not been specifically addressed herein but are, or will become, apparent from the description herein, the appended drawings and claims. All structural and functional equivalents to components of the above-described embodiments and additional embodiments as regarded by those of ordinary skill in the art are hereby expressly incorporated by reference and are intended to be encompassed by the present claims.

The methods that may be described above or claimed herein and any other methods which may fall within the scope of the appended claims can be performed in any desired suitable order and are not necessarily limited to any sequence described herein or as may be listed in the appended claims. Further, the methods of the present invention do not necessarily require use of the particular embodiments shown and described herein, but are equally applicable with any other suitable structure, form and configuration of components.

While exemplary embodiments of the invention have been shown and described, many variations, modifications and/or changes of the system, apparatus and methods of the present invention, such as in the components, details of construction and operation, arrangement of parts and/or methods of use, are possible, contemplated by the patent applicant(s), within the scope of the appended claims, and may be made and used by one of ordinary skill in the art without departing from the spirit or teachings of the invention and scope of appended claims. Thus, all matter herein set forth or shown in the accompanying drawings should be interpreted as illustrative, and the scope of the disclosure and the appended claims should not be limited to the embodiments described and shown herein. Furthermore, no component, method step or detail thereof made or shown in the present disclosure is intended to be dedicated to the public regardless of whether it is explicitly recited in the claims. In addition, the various changes and modifications in form, material and other details of the disclosed embodiments as may be apparent to those of ordinary skill in the art without departing from the spirit and scope of the present disclosure are also encompassed by the present disclosure.

The invention claimed is:

1. Apparatus for use in connection with receiving electroencephalographic (EEG) signals from a human subject's head through the scalp thereof, the apparatus comprising:
   a removable headset arranged and adapted to extend at least partially around the subject's head over at least part of the subject's scalp, said headset including an inner side and an outer side, said inner side being closest to the subject's scalp when said headset is positioned least partially around the subject's head,
   said headset further including a plurality of electrode stations and a plurality of intermediate portions extending between said electrode stations and shaped and sized to form open spaces therebetween, each said electrode station having an electrode aperture extending therethrough from said outer side to said inner side of said headset and, said headset further including a plurality of non-conductive biasing flaps, each said biasing flap being coupled to said headset and at least partially aligned over one of said electrode apertures, said headset further including at least one EEG signal transmission wire associated with said electrode stations for receiving EEG signals;
   a plurality of removable electrodes releasably engageable with said headset and useful to facilitate the transmission of EEG signals from the subject's head to at least one said EEG signal transmission wire of said headset during use of said headset, each said electrode including a top end, bottom end and at least one side extending therebetween, wherein each said electrode is configured to be releasably suspended within one of said electrode apertures and biased between said headset and the subject's head by said associated biasing flap; and
   a plurality of electrode covers constructed at least partially of flexible, liquid-absorbing material and arranged and adapted to be electrically-conductive, receive EEG signals from the subject's head and transmit such signals to at least one said EEG signal transmission wire of said headset during use of said headset, each said electrode cover at least partially encapsulating one said electrode and being laden with electrically-conductive liquid during use of said headset,
   wherein said each biasing flap is configured to bias said associated electrode cover into contact with the subject's head to allow said associated cover to receive EEG signals from the subject's head.

2. The apparatus of claim 1 further including an electrically-conductive ring disposed within each said electrode aperture, constructed at least partially of electrically-conductive material and electrically coupled to at least one said EEG signal transmission wire of said headset, wherein during use of said headset, each said electrically-conductive ring is arranged and adapted to receive EEG signals from said associated electrode cover and transmit such signals to said at least one said EEG signal transmission wire of said headset.

3. The apparatus of claim 2 wherein each said electrode cover includes a side surface and a bottom end that is electrically-conductive to said side surface, wherein said bottom end of each said electrode cover is arranged and adapted to electrically-conductively engage the subject's head to receive EEG signals therefrom and said side surface of each said electrode cover is arranged and adapted to slideably, conductively engage said associated electrically-conductive ring to transmit the EEG signals received from the subject's head to said electrically-conductive ring during use of said headset.

4. The apparatus of claim 1 wherein each said electrode cover includes a bottom end, said bottom end of each said electrode cover being configured to be scraped against and exfoliate the subject's scalp during use of said headset.

5. The apparatus of claim 1 wherein each said electrode cover is constructed at least partially of at least one among the group consisting of natural fabric, natural fibers, synthetic fabric, synthetic fibers and exfoliating material.

6. The apparatus of claim 1 wherein each said electrode cover is constructed and configured to provide sufficient surface contact with the subject's scalp during use of the headset to receive acceptable EEG signals from the subject's head.

7. The apparatus of claim 1 wherein each said electrode cover is configured to contact the subject's head at a contact interface during use of said headset, further wherein said intermediate portions of said headset and said open spaces therebetween are arranged and adapted to allow said contact interfaces to be viewable by the naked eye during use of said headset.

8. The apparatus of claim 7 wherein said intermediate portions of said headset are configured to flex to assist in conforming said headset to the shape of the subject's head and allow said contact interfaces to be viewable by the naked eye during use of said headset.

9. The apparatus of claim 1 wherein each said electrode is a unitary member entirely encapsulated by its said associated electrode cover to form an electrode-cover combination, further wherein each said electrode-cover combination is disposable.

10. The apparatus of claim 1 wherein said electrically-conductive liquid includes at least one among the group consisting of hair conditioner and optical contact lens solution.

11. The apparatus of claim 1 wherein said intermediate portions of said headset are constructed at least partially of at least one among the group consisting of rubber, foam rubber, silicon, closed-cell resin material, closed-cell copolymer material, biostatic material and antimicrobial material.

12. The apparatus of claim 1 wherein at least some of said intermediate portions of said headset include at least one flex point formed therein to assist in conforming said headset to the shape of the subject's head during use of said headset.

13. The apparatus of claim 1 wherein each said biasing flap is constructed at least partially of resilient material, further including first and second flap fasteners associated with each said biasing flap and adapted to releasably secure said associated biasing flap to said headset on opposite sides of said associated electrode aperture.

14. The apparatus of claim 1 wherein each said electrode includes at least one protrusion extending outwardly from at least one said side of said associated electrode, said protrusion being arranged and adapted to selectively position said electrode relative to said associated electrode aperture.

15. The apparatus of claim 14 wherein each said electrode has a cylindrical shape, further wherein said at least one protrusion comprises a circular ridge extending at least partially around the outer circumference of said associated electrode, further wherein said electrode cover is configured to conform to the shape of said at least one protrusion of said associated electrode.

16. The apparatus of claim 14 further including an electrode retention ring disposed within at least one among the group consisting of said electrode aperture and said biasing flap associated with each said electrode station, each said electrode retention ring having an upper edge facing said outer side of said headset and a lower edge facing said inner side of said headset.

17. The apparatus of claim 16 wherein each said biasing flap includes a flap hole at least partially aligned over said associated electrode aperture, further wherein each said associated electrode retention ring is disposed within said flap hole of said associated biasing flap, further wherein each said electrode retention ring includes at least one groove configured to selectively retain said at least one protrusion of said associated electrode, whereby when said at least one protrusion is selectively secured in said groove of said associated biasing flap, said electrode is configured to be moveable with said biasing flap relative to said electrode aperture and the subject's head during use of said headset.

18. The apparatus of claim 17 further including a plurality of electrically-conductive rings, one of said electrically-conductive rings being disposed within each said electrode aperture, each said electrically-conductive ring being electrically coupled to at least one said EEG signal transmission wire of said headset and useful to facilitate the transmission of EEG signals from said associated electrode cover to said at least one EEG signal transmission wire.

19. The apparatus of claim 16 wherein each said biasing flap is coupled to said outer side of said headset over said associated electrode aperture and configured to abut and apply biasing forces to said top end of said associated electrode.

20. The apparatus of claim 16 wherein one of said electrode retention rings is disposed within each said electrode aperture, constructed at least partially of electrically-conductive material, electrically coupled to at least one said EEG signal transmission wire of said headset and wherein during use of said headset, each said electrode retention ring is arranged and adapted to receive EEG signals from said associated electrode cover and transmit such signals to said at least one said EEG signal transmission wire of said headset, further wherein each said electrode is movable relative to said headset between at least one retracted position and at least one extended position, each said electrode in said retracted and extended positions being biased by said associated biasing flap in the direction of the subject's head during use of said headset, wherein when any said electrode is in at least one said retracted position, said at least one protrusion of said electrode is positioned closer to said upper edge of said retention ring than said lower edge of said retention ring, and when any said electrode is in said at least one extended position, said at least one protrusion of said electrode is positioned closer to said lower edge of said retention ring than said upper edge of said retention ring.

21. The apparatus of claim 20 wherein each said electrode is configured to be moveable within a distinct range of said retracted positions and a distinct range of said extended positions.

22. The apparatus of claim 1 wherein each said biasing flap includes a flap hole at least partially aligned over said associated electrode aperture, further wherein each said electrode is sized and configured to be releasably engaged with said headset by insertion into one of said flap holes and said associated electrode aperture from said outer side of said headset and removed from said headset by being moved through said associated flap hole and said associated electrode aperture in the direction of said inner side of said headset.

23. The apparatus of claim 1 wherein each said electrode is sized and configured to be releasably engaged with said headset by insertion into one of said electrode apertures from said inner side of said headset and removed from said headset by being moved through said associated electrode aperture in the direction of said inner side of said headset.

24. A method of using the apparatus of claim 1, the method comprising:
releasably suspending the plurality of electrodes along with their associated electrically-conductive, liquid laden, electrode covers within the respective associated electrode apertures in the headset;

placing the headset on the subject's head;

at least some of the biasing flaps biasing their associated electrodes in the direction of the subject's head independent of the other electrodes in the headset; and at least some of the electrode covers receiving useful signals from the subject's head and transmitting the received signals to at least one EEG signal transmission wire in the headset.

25. The method of claim 24 wherein each electrode is moveable between at least one retracted position and at least one extended position, the top end of each electrode in an extended position being closer to the outer side of the headset than the position of the top end of the electrode relative to the outer side of the headset in a retracted position, further including selectively, independently positioning each electrode in at least one retracted position, and if any of the respective electrode covers is not receiving useful signals from the subject's head, selectively, independently moving each such electrode from at least one retracted position to at least one extended position.

26. Apparatus for use in connection with receiving electroencephalographic (EEG) signals from a human subject's head through the scalp thereof, the apparatus comprising:

a removable headset arranged and adapted to extend at least partially around the subject's head over at least part of the subject's scalp, said headset including an inner side and an outer side, said inner side being closest to the subject's scalp when said headset is positioned least partially around the subject's head, said headset further including a plurality of electrode stations and a plurality of intermediate portions extending between said electrode stations and shaped and sized to form open spaces therebetween, each said electrode station having an electrode aperture extending therethrough from said outer side to said inner side of said headset, said headset further including a plurality of non-conductive biasing flaps, each said biasing flap being coupled to said headset and at least partially aligned over one of said electrode apertures, said headset further including at least one EEG signal transmission wire associated with said electrode stations for receiving EEG signals; and a plurality of removable electrodes releasably engageable with said headset and useful to facilitate the transmission of EEG signals from the subject's head to at least one said EEG signal transmission wire of said headset during use of said headset, each said electrode including a top end, bottom end, at least one side extending therebetween and at least one protrusion extending outwardly from said at least one side, said protrusion being arranged and adapted to selectively position said associated electrode relative to said associated electrode aperture, wherein each said electrode is configured to be releasably suspended within one of said electrode apertures and biased towards the subject's head by said associated biasing flap.

27. The apparatus of claim 26 wherein each said biasing flap includes a flap hole at least partially aligned over said associated electrode aperture, further wherein each said flap hole includes at least one groove configured to selectively retain said at least one protrusion of said associated electrode, whereby when said at least one protrusion is selectively secured in said groove of said associated biasing flap, said electrode is configured to be moveable with said biasing flap relative to said electrode aperture during use of said headset.

28. The apparatus of claim 27 wherein each said electrode is sized and configured to be releasably engaged with said headset by insertion into one of said flap holes and said associated electrode aperture from said outer side of said headset and removed from said headset by being moved through said associated flap hole and said associated electrode aperture in the direction of said inner side of said headset.

29. The apparatus of claim 26 wherein each said biasing flap is coupled to said outer side of said headset over said associated electrode aperture and configured to abut and apply biasing forces to said top end of said associated electrode, further wherein each said electrode is movable relative to said headset between at least one retracted position and at least one extended position, each said electrode in said retracted and extended positions being biased by said associated biasing flap in the direction of the subject's head during use of said headset, wherein when any said electrode is in at least one said retracted position, said at least one protrusion of said electrode is positioned closer to said outer side of said headset than said inner side of said headset, and when any said electrode is in said at least one extended position, said at least one protrusion of said electrode is positioned closer to said inner side of said headset than said outer side of said headset.

30. The apparatus of claim 29 wherein each said electrode is configured to be moveable within a distinct range of said retracted positions and a distinct range of said extended positions.

31. The apparatus of claim 26 further including an electrode retention ring disposed within at least one among the group consisting of said electrode aperture and said biasing flap associated with each said electrode station, each said electrode retention ring having an upper edge facing said outer side of said headset and a lower edge facing said inner side of said headset, further wherein each said electrode is movable relative to said headset between at least one retracted position and at least one extended position, each said electrode in said retracted and extended positions being biased by said associated biasing flap in the direction of the subject's head during use of said headset, wherein when any said electrode is in at least one said retracted position, said at least one protrusion of said electrode is positioned closer to said upper edge of said retention ring than said lower edge of said retention ring, and when any said electrode is in said at least one extended position, said at least one protrusion of said electrode is positioned closer to said lower edge of said retention ring than said upper edge of said retention ring.

32. The apparatus of claim 26 further including a plurality of electrode covers constructed at least partially of flexible, liquid-absorbing material and arranged and adapted to be electrically-conductive, receive EEG signals from the subject's head and transmit such signals to at least one said EEG signal transmission wire of said headset during use of said headset, each said electrode cover at least partially encapsulating one said electrode and being laden with electrically-conductive liquid during use of said headset, wherein said each biasing flap is configured to bias said associated electrode cover into contact with the subject's head to allow said associated cover to receive EEG signals from the subject's head.

33. The apparatus of claim 32 further including an electrically-conductive ring disposed within each said electrode aperture, constructed at least partially of electrically-conductive material and electrically coupled to at least one said EEG signal transmission wire of said headset, wherein during use of said headset, each said electrically-conductive ring is arranged and adapted to receive EEG signals from said associated electrode cover and transmit such signals to said at least one said EEG signal transmission wire of said headset.

34. The apparatus of claim 32 wherein each said electrode has a cylindrical shape, further wherein said at least one protrusion comprises a circular ridge extending at least partially around the outer circumference of said associated electrode, further wherein said electrode cover is configured to conform to the shape of said at least one protrusion of said associated electrode.

35. A method of using the apparatus of claim 26, the method comprising:
  releasably suspending the plurality of electrodes within the respective associated electrode apertures in the headset;
  placing the headset on the subject's head; and
  at least some of the biasing flaps biasing their associated electrodes in the direction of the subject's head independent of the other electrodes in the headset.

36. Apparatus for use in connection with receiving electroencephalographic (EEG) signals from a human subject's head through the scalp thereof, the apparatus comprising:
  a removable headset arranged and adapted to extend at least partially around the subject's head over at least part of the subject's scalp, said headset including an inner side and an outer side, said inner side being closest to the subject's scalp when said headset is positioned least partially around the subject's head,
  said headset further including a plurality of electrode stations and a plurality of intermediate portions extending between said electrode stations and shaped and sized to form open spaces therebetween, each said electrode station having an electrode aperture extending therethrough from said outer side to said inner side of said headset, said headset further including a plurality of biasing flaps, each said biasing flap being coupled to said headset and at least partially aligned over one of said electrode apertures, said headset further including at least one EEG signal transmission wire associated with said electrode stations for receiving EEG signals; and
  a plurality of removable electrodes releasably engageable with said headset and useful to facilitate the transmission of EEG signals from the subject's head to at least one said EEG signal transmission wire of said headset during use of said headset, each said electrode including a top end, bottom end, at least one side extending therebetween and at least one protrusion extending outwardly from said at least one side, said protrusion being arranged and adapted to selectively position said associated electrode relative to said associated electrode aperture, wherein each said electrode is configured to be releasably suspended within one of said electrode apertures and biased towards the subject's head by said associated biasing flap, further wherein each said biasing flap includes a flap hole at least partially aligned over said associated electrode aperture, each said flap hole including at least one groove configured to selectively retain at least one said protrusion of said associated electrode,
  whereby when at least one protrusion is selectively secured in said groove of said associated biasing flap, said electrode is configured to be moveable with said biasing flap relative to said electrode aperture during use of said headset.

37. Apparatus for use in connection with receiving electroencephalographic (EEG) signals from a human subject's head through the scalp thereof, the apparatus comprising:
  a removable headset arranged and adapted to extend at least partially around the subject's head over at least part of the subject's scalp, said headset including an inner side and an outer side, said inner side being closest to the subject's scalp when said headset is positioned least partially around the subject's head,
  said headset further including a plurality of electrode stations and a plurality of intermediate portions extending between said electrode stations and shaped and sized to form open spaces therebetween, each said electrode station having an electrode aperture extending therethrough from said outer side to said inner side of said headset, said headset further including a plurality of biasing flaps, each said biasing flap being directly coupled to said headset and at least partially aligned over one of said electrode apertures, said headset further including at least one EEG signal transmission wire associated with said electrode stations for receiving EEG signals;
  a plurality of removable electrodes releasably engageable with said headset and useful to facilitate the transmission of EEG signals from the subject's head to at least one said EEG signal transmission wire of said headset during use of said headset, each said electrode including a top end, bottom end and at least one side extending therebetween, wherein each said electrode is configured to be releasably suspended within one of said electrode apertures and biased between said headset and the subject's head by said associated biasing flap; and
  a plurality of electrode covers constructed at least partially of flexible, liquid-absorbing material and arranged and adapted to be electrically-conductive, receive EEG signals from the subject's head and transmit such signals to at least one said EEG signal transmission wire of said headset during use of said headset, each said electrode cover at least partially encapsulating one said electrode and being laden with electrically-conductive liquid during use of said headset, wherein said each biasing flap is configured to bias said associated electrode cover into contact with the subject's head to allow said associated cover to receive EEG signals from the subject's head.

38. The apparatus of claim 37 further including an electrically-conductive ring disposed within each said electrode aperture, constructed at least partially of electrically-conductive material and electrically coupled to at least one said EEG signal transmission wire of said headset, wherein during use of said headset, each said electrically-conductive ring is arranged and adapted to receive EEG signals from said associated electrode cover and transmit such signals to said at least one said EEG signal transmission wire of said headset.

39. The apparatus of claim 37 wherein each said electrode is a unitary member entirely encapsulated by its said associated electrode cover to form an electrode-cover combination, further wherein each said electrode-cover combination is disposable.

40. The apparatus of claim 37 wherein each said electrode includes at least one protrusion extending outwardly from at least one said side of said associated electrode, said protrusion being arranged and adapted to selectively position said electrode relative to at least one among the group consisting of said associated electrode aperture and the subject's head.

41. The apparatus of claim 40 further including an electrode retention ring disposed within at least one among the group consisting of said electrode aperture and said biasing flap associated with each said electrode station, said electrode retention ring having an upper edge facing said outer side of said headset and a lower edge facing said inner side of said headset, further wherein each said electrode is movable relative to said headset between at least one retracted position and at least one extended position, each said electrode in said retracted and extended positions being biased by said associated biasing flap in the direction of the subject's head during use of said headset, wherein when any said electrode is in at least one said retracted position, said at least one protrusion of said electrode is positioned closer to said upper edge of said retention ring than said lower edge of said retention ring, and when any said electrode is in said at least one extended position, said at least one protrusion of said electrode is positioned closer to said lower edge of said retention ring than said upper edge of said retention ring.

42. The apparatus of claim 37 wherein each said biasing flap is coupled to said outer side of said headset over said associated electrode aperture and configured to abut and apply biasing forces to said top end of said associated electrode.

43. The apparatus of claim 37 wherein each said electrode is movable relative to said headset between at least one retracted position and at least one extended position, the top end of each said electrode in at least one said extended position being closer to said outer side of said headset than the position of said top end of said electrode relative to said outer side of said headset in said retracted position.

44. The apparatus of claim 43 wherein each said electrode is configured to be moveable within a distinct range of said retracted positions and a distinct range of said extended positions.

45. A method of using the apparatus of claim 37, the method comprising:
releasably suspending the plurality of electrodes along with their associated electrically-conductive, liquid laden, electrode covers within the respective associated electrode apertures in the headset;
placing the headset on the subject's head;
at least some of the biasing flaps biasing their associated electrodes in the direction of the subject's head independent of the other electrodes in the headset; and
at least some of the electrode covers receiving useful signals from the subject's head and transmitting the received signals to at least one EEG signal transmission wire in the headset.

46. The method of claim 45 wherein each electrode is moveable between at least one retracted position and at least one extended position, the top end of each electrode in an extended position being closer to the outer side of the headset than the position of the top end of the electrode relative to the outer side of the headset in a retracted position, further including
selectively, independently positioning each electrode in at least one retracted position, and
if any of the respective electrode covers is not receiving useful signals from the subject's head, selectively, independently moving each such electrode from at least one retracted position to at least one extended position.

47. Apparatus for use in connection with receiving electroencephalographic (EEG) signals from a human subject's head through the scalp thereof, the apparatus comprising:
a removable headset arranged and adapted to extend at least partially around the subject's head over at least part of the subject's scalp, said headset including an inner side and an outer side, said inner side being closest to the subject's scalp when said headset is positioned least partially around the subject's head,
said headset further including a plurality of electrode stations and a plurality of intermediate portions extending between said electrode stations and shaped and sized to form open spaces therebetween, each said electrode station having an electrode aperture extending therethrough from said outer side to said inner side of said headset,
said headset further including a plurality of biasing flaps and at least first and second flap fasteners associated with each said biasing flap, each said biasing flap being coupled to said-headset and at least partially aligned over one of said electrode apertures, said at least first and second flap fasteners being adapted to secure said associated biasing flap to said headset on opposite sides of said associated electrode aperture,
said headset further including at least one EEG signal transmission wire associated with said electrode stations for receiving EEG signals;
a plurality of removable electrodes releasably engageable with said headset and useful to facilitate the transmission of EEG signals from the subject's head to at least one said EEG signal transmission wire of said headset during use of said headset, each said electrode including a top end, bottom end and at least one side extending therebetween, wherein each said electrode is configured to be releasably suspended within one of said electrode apertures and biased between said headset and the subject's head by said associated biasing flap; and
a plurality of electrode covers constructed at least partially of flexible, liquid-absorbing material and arranged and adapted to be electrically-conductive, receive EEG signals from the subject's head and transmit such signals to at least one said EEG signal transmission wire of said headset during use of said headset, each said electrode cover at least partially encapsulating one said electrode and being laden with electrically-conductive liquid during use of said headset, wherein said each biasing flap is configured to bias said associated electrode cover into contact with the subject's head to allow said associated cover to receive EEG signals from the subject's head.

48. The apparatus of claim 47 further including an electrically-conductive ring disposed within each said electrode aperture, constructed at least partially of electrically-conductive material and electrically coupled to at least one said EEG signal transmission wire of said headset, wherein during use of said headset, each said electrically-conductive ring is arranged and adapted to receive EEG signals from said associated electrode cover and transmit such signals to said at least one said EEG signal transmission wire of said headset.

49. A method of using the apparatus of claim 47, the method comprising:
releasably suspending the plurality of electrodes along with their associated electrically-conductive, liquid laden, electrode covers within the respective associated electrode apertures in the headset;

placing the headset on the subject's head;

at least some of the biasing flaps biasing their associated electrodes in the direction of the subject's head independent of the other electrodes in the headset; and at least some of the electrode covers receiving useful signals from the subject's head and transmitting the received signals to at least one EEG signal transmission wire in the headset.

50. Apparatus for use in connection with receiving electroencephalographic (EEG) signals from a human subject's head through the scalp thereof, the apparatus comprising:

a removable headset arranged and adapted to extend at least partially around the subject's head over at least part of the subject's scalp, said headset including an inner side and an outer side, said inner side being closest to the subject's scalp when said headset is positioned least partially around the subject's head, said headset further including a plurality of electrode stations and a plurality of intermediate portions extending between said electrode stations and shaped and sized to form open spaces therebetween, each said electrode station having an electrode aperture extending therethrough from said outer side to said inner side of said headset, said headset further including a plurality of biasing flaps, each said biasing flap being directly coupled to said headset and at least partially aligned over one of said electrode apertures, said headset further including at least one EEG signal transmission wire associated with said electrode stations for receiving EEG signals; and a plurality of removable electrodes releasably engageable with said headset and useful to facilitate the transmission of EEG signals from the subject's head to at least one said EEG signal transmission wire of said headset during use of said headset, each said electrode including a top end, bottom end, at least one side extending therebetween and at least one protrusion extending outwardly from said at least one side, said protrusion being arranged and adapted to selectively position said associated electrode relative to said associated electrode aperture, wherein each said electrode is configured to be releasably suspended within one of said electrode apertures and biased towards the subject's head by said associated biasing flap.

51. The apparatus of claim 50 further including an electrode retention ring disposed within at least one among the group consisting of said electrode aperture and said biasing flap associated with each said electrode station, each said electrode retention ring having an upper edge facing said outer side of said headset and a lower edge facing said inner side of said headset, further wherein each said electrode is movable relative to said headset between at least one retracted position and at least one extended position, each said electrode in said retracted and extended positions being biased by said associated biasing flap in the direction of the subject's head during use of said headset, wherein when any said electrode is in at least one said retracted position, said at least one protrusion of said electrode is positioned closer to said upper edge of said retention ring than said lower edge of said retention ring, and when any said electrode is in said at least one extended position, said at least one protrusion of said electrode is positioned closer to said lower edge of said retention ring than said upper edge of said retention ring.

52. The apparatus of claim 50 further including a plurality of electrode covers constructed at least partially of flexible, liquid-absorbing material and arranged and adapted to be electrically-conductive, receive EEG signals from the subject's head and transmit such signals to at least one said EEG signal transmission wire of said headset during use of said headset, each said electrode cover at least partially encapsulating one said electrode and being laden with electrically-conductive liquid during use of said headset, wherein said each biasing flap is configured to bias said associated electrode cover into contact with the subject's head to allow said associated cover to receive EEG signals from the subject's head.

53. The apparatus of claim 52 further including an electrically-conductive ring disposed within each said electrode aperture, constructed at least partially of electrically-conductive material and electrically coupled to at least one said EEG signal transmission wire of said headset, wherein during use of said headset, each said electrically-conductive ring is arranged and adapted to receive EEG signals from said associated electrode cover and transmit such signals to said at least one said EEG signal transmission wire of said headset.

54. A method of using the apparatus of claim 50, the method comprising:

releasably suspending the plurality of electrodes within the respective associated electrode apertures in the headset;

placing the headset on the subject's head; and at least some of the biasing flaps biasing their associated electrodes in the direction of the subject's head independent of the other electrodes in the headset.

55. Apparatus for use in connection with receiving electroencephalographic (EEG) signals from a human subject's head through the scalp thereof, the apparatus comprising:

a removable headset arranged and adapted to extend at least partially around the subject's head over at least part of the subject's scalp, said headset including an inner side and an outer side, said inner side being closest to the subject's scalp when said headset is positioned least partially around the subject's head, said headset further including a plurality of electrode stations and a plurality of intermediate portions extending between said electrode stations and shaped and sized to form open spaces therebetween, each said electrode station having an electrode aperture extending therethrough from said outer side to said inner side of said headset, said headset further including a plurality of biasing flaps and at least first and second flap fasteners associated with each said biasing flap, each said biasing flap being coupled to said headset and at least partially aligned over one of said electrode apertures, said at least first and second flap fasteners being adapted to secure said associated biasing flap to said headset on opposite sides of said associated electrode aperture, said headset further including at least one EEG signal transmission wire associated with said electrode stations for receiving EEG signals; and a plurality of removable electrodes releasably engageable with said headset and useful to facilitate the transmission of EEG signals from the subject's head to at least one said EEG signal transmission wire of said headset during use of said headset, each said electrode including a top end, bottom end, at least one side extending therebetween and at least one protrusion extending outwardly from said at least one side, said protrusion being arranged and adapted to selectively position said associated electrode relative to said associated electrode aperture, wherein each said electrode is configured to be releasably suspended within one of said electrode apertures and biased towards the subject's head by said associated biasing flap.

56. The apparatus of claim 55 further including an electrode retention ring disposed within at least one among the group consisting of said electrode aperture and said biasing flap associated with each said electrode station, each said electrode retention ring having an upper edge facing said outer side of said headset and a lower edge facing said inner side of said headset, further wherein each said electrode is movable relative to said headset between at least one retracted position and at least one extended position, each said electrode in said retracted and extended positions being biased by said associated biasing flap in the direction of the subject's head during use of said headset, wherein when any said electrode is in at least one said retracted position, said at least one protrusion of said electrode is positioned closer to said upper edge of said retention ring than said lower edge of said retention ring, and when any said electrode is in said at least one extended position, said at least one protrusion of said electrode is positioned closer to said lower edge of said retention ring than said upper edge of said retention ring.

57. The apparatus of claim 55 further including a plurality of electrode covers constructed at least partially of flexible, liquid-absorbing material and arranged and adapted to be electrically-conductive, receive EEG signals from the subject's head and transmit such signals to at least one said EEG signal transmission wire of said headset during use of said headset, each said electrode cover at least partially encapsulating one said electrode and being laden with electrically-conductive liquid during use of said headset, wherein said each biasing flap is configured to bias said associated electrode cover into contact with the subject's head to allow said associated cover to receive EEG signals from the subject's head.

58. The apparatus of claim 57 further including an electrically-conductive ring disposed within each said electrode aperture, constructed at least partially of electrically-conductive material and electrically coupled to at least one said EEG signal transmission wire of said headset, wherein during use of said headset, each said electrically-conductive ring is arranged and adapted to receive EEG signals from said associated electrode cover and transmit such signals to said at least one said EEG signal transmission wire of said headset.

59. A method of using the apparatus of claim 55, the method comprising:
 releasably suspending the plurality of electrodes within the respective associated electrode apertures in the headset;
 placing the headset on the subject's head; and
 at least some of the biasing flaps biasing their associated electrodes in the direction of the subject's head independent of the other electrodes in the headset.

* * * * *